United States Patent
Glombik et al.

(10) Patent No.: US 8,101,583 B2
(45) Date of Patent: Jan. 24, 2012

(54) 1,4-BENZOTHIEPIN-1,1-DIOXIDE DERIVATIVES WHICH ARE SUBSTITUTED WITH FLUORINE, METHOD FOR PRODUCING THE SAME, DRUGS CONTAINING SAID COMPOUNDS AND USE THEREOF

(75) Inventors: Heiner Glombik, Hofheim (DE); Wendelin Frick, Hunstetten-Beuerbach (DE); Stefan Theis, Frankfurt (DE); Hubert Heuer, Schwabenheim (DE); Hans-Ludwig Schaefer, Hochheim (DE); Werner Kramer, Mainz-Laubenheim (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 265 days.

(21) Appl. No.: 12/465,928

(22) Filed: May 14, 2009

(65) Prior Publication Data

US 2010/0062991 A1    Mar. 11, 2010

Related U.S. Application Data

(63) Continuation of application No. PCT/EP2007/009395, filed on Oct. 30, 2007.

(30) Foreign Application Priority Data

Nov. 14, 2006 (DE) .................. 10 2006 053 637

(51) Int. Cl.
*C07D 281/10* (2006.01)
*A61K 31/55* (2006.01)
*A61K 31/70* (2006.01)

(52) U.S. Cl. ............. 514/43; 514/23; 514/42; 536/22.1; 536/29.1; 536/29.13

(58) Field of Classification Search .................. None
See application file for complete search history.

(56) References Cited

U.S. PATENT DOCUMENTS

| 5,994,391 | A | 11/1999 | Lee et al. | |
| 7,615,536 | B2 * | 11/2009 | Frick et al. | 514/43 |
| 2004/0087648 | A1 * | 5/2004 | Frick et al. | 514/431 |

FOREIGN PATENT DOCUMENTS

| WO | WO 03/018024 | 3/2003 |
| WO | WO 03/040127 | 5/2003 |
| WO | WO 2004/052903 | 6/2004 |
| WO | WO 2004/076430 | 9/2004 |
| WO | WO 2005/121161 | 12/2005 |
| WO | WO 2007/009655 | 1/2007 |

OTHER PUBLICATIONS

Vippagunta et al., Advanced Drug Delivery, 2001 (48) 3-26.*

* cited by examiner

*Primary Examiner* — Traviss C McIntosh, III
(74) *Attorney, Agent, or Firm* — Scully, Scott, Murphy & Presser, P.C.

(57) ABSTRACT

This invention relates to Novel 1,4-benzothiepin-1,1-dioxide derivatives which are substituted with fluorine, method for producing the same, drugs containing said compounds and use thereof.

18 Claims, No Drawings

1,4-BENZOTHIEPIN-1,1-DIOXIDE DERIVATIVES WHICH ARE SUBSTITUTED WITH FLUORINE, METHOD FOR PRODUCING THE SAME, DRUGS CONTAINING SAID COMPOUNDS AND USE THEREOF

Novel 1,4-benzothiepin-1,1-dioxide derivatives which are substituted with fluorine, method for producing the same, drugs containing said compounds and use thereof The invention relates to fluorine-substituted 1,4-benzothiepin 1,1-dioxide derivatives and the physiologically tolerated salts thereof.

1,4-Benzothiepin 1,1-dioxide derivatives of similar structure have previously been described (U.S. Pat. No. 5,994,391).

The invention was based on the object of providing further compounds which show a hypolipidemic effect.

The invention therefore relates to the compound of the formula I

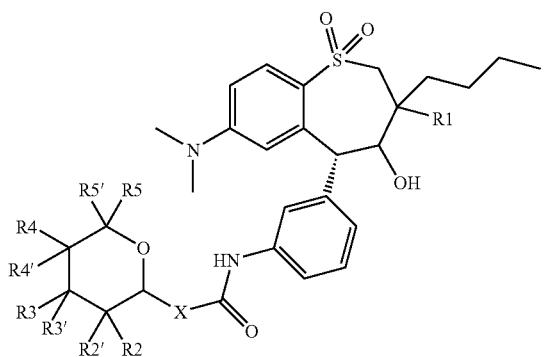

in which the meanings are
X O, NH, $CH_2$ or a bond;
R1 ($C_1$-$C_6$)-alkyl;
R2, R2', R3, R3', R4, R4', R5, R5' independently of one another H, F, Cl, Br, I, OH, —($CH_2$)—OH, $CH_2F$, $CHF_2$, $CF_3$, $NO_2$, $N_3$, CN, $S(O)_p$—R6, ($C_1$-$C_6$)-alkylene-$S(O)_p$—R6, COOH, COO($C_1$-$C_6$)alkyl, $CONH_2$, CONH($C_1$-$C_6$)alkyl, CON[($C_1$-$C_6$)alkyl]$_2$, ($C_1$-$C_6$)-alkyl, ($C_2$-$C_6$)-alkenyl, ($C_2$-$C_6$)-alkynyl, O—($C_1$-$C_6$)-alkyl, where one, more than one, or all hydrogen(s) in the alkyl radicals may be replaced by fluorine;
phenyl, —($CH_2$)-phenyl, —($CH_2$)$_n$-phenyl, O-phenyl, O—($CH_2$)$_m$-phenyl, —($CH_2$)—O—($CH_2$)$_m$-phenyl, where the phenyl ring may be substituted one to 3 times by F, Cl, Br, I, OH, $CF_3$, $NO_2$, ON, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COOO—($C_1$-$C_6$)-alkyl, $CONH_2$;
where always at least one of the radicals R2, R2', R3, R3', R4, R4' has the meaning of fluorine or R5, R5' has the meaning of $CH_2F$, $CHF_2$ or $CF_3$;
R6 H, OH, ($C_1$-$C_6$)-alkyl, $NH_2$, NH($C_1$-$C_6$)-alkyl, N(($C_1$-$C_6$)-alkyl)$_2$;
n 2, 3, 4, 5, 6;
m 1, 2, 3, 4, 5, 6;
p 0, 1, 2;
and the pharmaceutically acceptable salts thereof.

Preference is given to compounds of the formula I in which the meanings are
X NH;
R1 ($C_1$-$C_6$)-alkyl;
R2, R2', R3, R3', R4, R4', R5, R5' independently of one another H, F, Cl, Br, I, OH, —($CH_2$)—OH, $CH_2F$, $CHF_2$, $CF_3$, $NO_2$, $N_3$, CN, $S(O)_p$—R6, ($C_1$-$C_6$)-alkylene-$S(O)_p$—R6, COOH, COO($C_1$-$C_6$)alkyl, $CONH_2$, CONH($C_1$-$C_6$)alkyl, CON[($C_1$-$C_6$)alkyl]$_2$, ($C_1$-$C_6$)-alkyl, ($C_2$-$C_6$)-alkenyl, ($C_2$-$C_6$)-alkynyl, O—($C_1$-$C_6$)-alkyl, where one, more than one, or all hydrogen(s) in the alkyl radicals may be replaced by fluorine;
phenyl, —($CH_2$)-phenyl, —($CH_2$)$_n$-phenyl, O-phenyl, O—($CH_2$)$_m$-phenyl, —($CH_2$)—O—($CH_2$)$_m$-phenyl, where the phenyl ring may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COOO—($C_1$-$C_6$)-alkyl, $CONH_2$;
where always at least one of the radicals R2, R2', R3, R3', R4, R4' has the meaning of fluorine or R5, R5' has the meaning of $CH_2F$, $CHF_2$ or $CF_3$;
R6 H, OH, ($C_1$-$C_6$)-alkyl, $NH_2$, NH($C_1$-$C_6$)-alkyl, N(($C_1$-$C_6$)-alkyl)$_2$;
n 2, 3, 4, 5, 6;
m 1, 2, 3, 4, 5, 6;
p 0, 1, 2;
and the pharmaceutically acceptable salts thereof.

Particular preference is given to compounds of the formula I in which the meanings are
X NH;
R1 ($C_1$-$C_6$)-alkyl;
R4 F;
R4' H, F;
R2, R2', R3, R3', R5, R5' independently of one another H, F, Cl, Br, I, OH, —($CH_2$)—OH, $CH_2F$, $CHF_2$, $CF_3$, $NO_2$, $N_3$, CN, $S(O)_p$—R6, ($C_1$-$C_6$)-alkylene-$S(O)_p$—R6, COOH, COO($C_1$-$C_6$)alkyl, $CONH_2$, CONH($C_1$-$C_6$)alkyl, CON[($C_1$-$C_6$)alkyl]$_2$, ($C_1$-$C_6$)-alkyl, ($C_2$-$C_6$)-alkenyl, ($C_2$-$C_6$)-alkynyl, O—($C_1$-C6)-alkyl, where one, more than one, or all hydrogen(s) in the alkyl radicals may be replaced by fluorine;
phenyl, —($CH_2$)-phenyl, —($CH_2$)$_n$-phenyl, O-phenyl, O—($CH_2$)$_m$-phenyl, —($CH_2$)—O—($CH_2$)$_m$-phenyl, where the phenyl ring may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$;
R6 H, OH, ($C_1$-$C_6$)-alkyl, $NH_2$, NH($C_1$-$C_6$)-alkyl, N(($C_1$-$C_6$)-alkyl)$_2$;
n 2, 3, 4, 5, 6;
m 1, 2, 3, 4, 5, 6;
p 0, 1, 2;
and the pharmaceutically acceptable salts thereof.

Preference is further given to compounds of the formula I in which one, two or three of the radicals R2, R2', R3, R3', R4, R4', R5, R5' have the meaning of OH.

Compounds of the formula I preferred in one embodiment are those in which the radical X is O.

Compounds of the formula I preferred in one embodiment are those in which the radical X is NH.

Compounds of the formula I preferred in one embodiment are those in which the radical X is $CH_2$.

Compounds of the formula I preferred in one embodiment are those in which the radical R1 is butyl.

Compounds of the formula I preferred in one embodiment are those in which the radical R1 is ethyl.

Compounds of the formula I preferred in one embodiment are those in which the radical at least one of the radicals R2, R2', R3, R3', R4, R4', R5, R5', R6 or R6' is $CH_2OH$.

Compounds of the formula I preferred in one embodiment are those in which the radical at least one of the radicals R2, R2', R3, R3', R4, R4', R5, R5', R6 or R6' is $CH_2OSO_3H$.

Compounds of the formula I preferred in one embodiment are those in which the radical at least one of the radicals R5 or R5' is $CH_2OH$.

Compounds of the formula I preferred in one embodiment are those in which the radical at least one of the radicals R5 or R5' is $CH_2OSO_3H$.

Compounds of the formula I preferred in one embodiment are those in which the structure of the formula I is as follows:

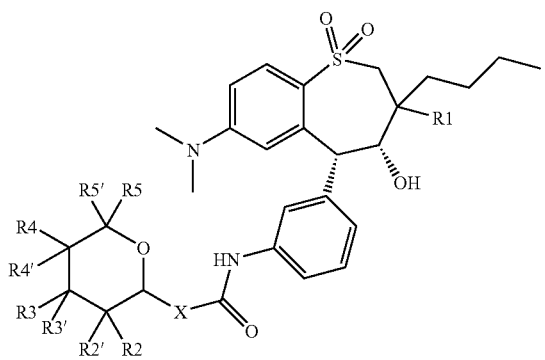

If radicals or substituents may occur more than once in the compounds of the formulae I, they may all independently of one another have the stated meaning and be identical or different.

The alkyl, alkenyl, alkynyl, alkylene, alkenylene and alkynylene radicals in the radicals R1, R2, R2', R3, R3', R4, R4', R5, R5' and R6 may be either straight-chain or branched.

The invention relates to compounds of the formula I in the form of their tautomers, racemates, racemic mixtures, mixtures of stereoisomers, pure stereoisomers, mixtures of diastereoisomers and pure diastereoisomers. The mixtures are separated for example by chromatographic means.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acids, and organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acids. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for preparing or purifying pharmaceutically acceptable salts and/or for use in nontherapeutic, for example in vitro applications.

The compounds of the invention may also exist in various polymorphous forms, e.g. as amorphous and crystalline polymorphous forms. All polymorphous forms of the compounds according to the invention belong within the framework of the invention and are a further aspect of the invention.

All references to "compound(s) of formula I" hereinafter refer to compound(s) of the formula I as described hereinabove, and the salts thereof as described herein.

An alkyl radical means a straight-chain or branched hydrocarbon chain having up to eight carbons, such as, for example, methyl, ethyl, isopropyl, tert-butyl, hexyl, heptyl, octyl. The alkyl radicals may be substituted once or more than once as described above.

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The compound(s) of the formula I can also be administered in combination with further active ingredients.

The amount of a compound of formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg and 50 mg) per day and per kilogram of body weight, for example 3-10 mg/kg/day. An intravenous dose may be for example in the range from 0.3 mg to 1.0 mg/kg, which can suitably be administered as infusion of from 10 ng to 100 ng per kilogram per minute. Suitable infusion solutions for these purposes may comprise for example from 0.1 ng to 10 mg, typically from 1 ng to 10 mg, per milliliter. Single doses may comprise for example from 1 mg to 10 g of the active ingredient. Thus, ampules for injections may comprise for example from 1 mg to 100 mg, and single-dose formulations which can be administered orally, such as, for example, tablets or capsules, may comprise for example from 1.0 to 1000 mg, typically from 10 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contains a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

Further active ingredients suitable for combination products are: All antidiabetics which are mentioned in the Rote Liste 2006, chapter 12; all weight-reducing agents/appetite suppressants which are mentioned in the Rote Liste 2006, chapter 1; all lipid-lowering agents which are mentioned in the Rote Liste 2006, chapter 58. They may be combined with the compound of the invention of the formula I in particular for a synergistic improvement in the effect. The active ingredient combination can be administered either by separate administration of the active ingredients to the patient or in the form of combination products in which a plurality of active ingredients is present in a pharmaceutical preparation. Most of the active ingredients mentioned hereinafter are disclosed in the USP Dictionary of USAN and International Drug Names, US Pharmacopeia, Rockville 2001.

Antidiabetics include insulin and insulin derivatives such as, for example, Lantus® (see www.lantus.com) or HMR 1964 or Levemir® (insulin detemir) or those described in WO2005005477 (Novo Nordisk), fast-acting insulins (see U.S. Pat. No. 6,221,633), inhalable insulins such as, for example, Exubera® or oral insulins such as, for example, IN-105 (Nobex) or Oral-lyn™ (Generex Biotechnology), GLP-1 derivatives such as, for example, exenatide, liraglutide or those which have been disclosed in WO 98/08871, WO2005027978, WO2006037811 or WO2006037810 of Novo Nordisk A/S, in WO 01/04156 of Zealand or in WO 00/34331 of Beaufour-Ipsen, pramlintide acetate (Symlin; Amylin Pharmaceuticals), and orally effective hypoglycemic active ingredients.

The orally effective hypoglycemic active ingredients include preferably
sulfonylureas,
biguanidines,
meglitinides,
oxadiazolidinediones,
thiazolidinediones,
glucosidase inhibitors,
inhibitors of glycogen phosphorylase,
glucagon antagonists,
glucokinase activators,
inhibitors of fructose-1,6-bisphosphatase,
modulators of glucose transporter 4 (GLUT4),
inhibitors of glutamine-fructose-6-phosphate amidotransferase (GFAT),
GLP-1 agonists, potassium channel openers such as, for example, those which have been disclosed in WO 97/26265 and WO 99/03861 of Novo Nordisk A/S, or those which are described in WO2006045799 (Solvay),
inhibitors of dipeptidylpeptidase IV (DPP-IV),
insulin sensitizers,
inhibitors of liver enzymes involved in stimulating gluconeogenesis and/or glycogenolysis, modulators of glucose uptake, of glucose transport and of glucose reabsorption,
inhibitors of 11β-HSD1,
inhibitors of protein tyrosine phosphatase 1B (PTP1B),
modulators of the sodium-dependent glucose transporter 1 or 2 (SGLT1, SGLT2),
compounds which alter lipid metabolism such as antihyperlipidemic active ingredients and antilipidemic active ingredients,
compounds which reduce food intake,
compounds which increase thermogenesis,
PPAR and RXR modulators and
active ingredients which act on the ATP-dependent potassium channel of the beta cells.

In one embodiment of the invention, the compounds of the formula I is administered in combination with an HMGCoA reductase inhibitor such as simvastatin, fluvastatin, pravastatin, lovastatin, atorvastatin, cerivastatin, rosuvastatin or L-659699.

In one embodiment of the invention, the compound of the formula I is administered in combination with a cholesterol absorption inhibitor such as, for example, ezetimibe, tiqueside, pamaqueside, FM-VP4 (sitostanol/campesterol ascorbyl phosphate; Forbes Medi-Tech, WO2005042692, WO2005005453), MD-0727 (Microbia Inc., WO2005021497, WO2005021495) or with compounds as described in WO2002066464 (Kotobuki Pharmaceutical Co. Ltd.), or WO2005044256 or WO2005062824 (Merck & Co.) or WO2005061451 and WO2005061452 (AstraZeneca AB), and WO2006017257 (Phenomix) or WO2005033100 (Lipideon Biotechnology AG).

In one embodiment of the invention, the compound of the formula I is administered in combination with Vytorin™, a fixed combination of ezetimibe and simvastatin.

In one embodiment of the invention, the compound of the formula I is administered in combination with a fixed combination of ezetimibe with fenofibrate.

In a further embodiment of the invention, the compound of the formula I is administered in combination with a fixed combination of fenofibrate and rosuvastatin.

In one embodiment of the invention, the compound of the formula I is administered in combination with ISIS-301012, an antisense oligonucleotide able to regulate the apolipoprotein B gene.

In one embodiment of the invention, the compound of the formula I is administered in combination with a PPAR gamma agonist such as, for example, rosiglitazone, pioglitazone, JTT-501, GI 262570, R-483, CS-011 (rivoglitazone).

In one embodiment of the invention, the compound of the formula I is administered in combination with Competact™, a fixed combination of pioglitazone hydrochloride with metformin hydrochloride.

In one embodiment of the invention, the compound of the formula I is administered in combination with duetact™, a fixed combination of pioglitazone hydrochloride with glimepiride.

In one embodiment of the invention, the compound of the formula I is administered in combination with Avandamet®, a fixed combination of rosiglitazone maleate with metformin hydrochloride.

In one embodiment of the invention, the compound of the formula I is administered in combination with a PPAR alpha agonist such as, for example, GW9578, GW-590735, K-111, LY-674, KRP-101, DRF-10945.

In one embodiment of the invention, the compound of the formula I is administered in combination with a mixed PPAR alpha/gamma agonist such as, for example, naveglitazar, LY-510929, ONO-5129, E-3030, AVE 8042, AVE 8134, AVE 0847, or as described in PCT/US 00/11833, PCT/US 00/11490, DE10142734.4 or in J. P. Berger et al., TRENDS in Pharmacological Sciences 28(5), 244-251, 2005.

In one embodiment of the invention, the compound of the formula I is administered in combination with a PPAR delta agonist such as, for example, GW-501516.

In one embodiment, the compound of the formula I is administered in combination with metaglidasen or with MBX-2044 or other partial PPAR gamma agonists/antagonists.

In a further embodiment of the invention, the compound of the formula I is administered in combination with an activator of AMP-activated protein kinase (AMPK) such as, for example, A-769662 or those compounds described in US 20050038068.

In one embodiment of the invention, the compound of the formula I is administered in combination with a fibrate such as, for example, fenofibrate, clofibrate or bezafibrate.

In one embodiment of the invention, the compound of the formula I is administered in combination with an MTP inhibitor such as, for example, implitapide, BMS-201038, R-103757 or those described in WO2005085226, WO2005121091, WO2006010423.

In one embodiment of the invention, the compound of the formula I is administered in combination with a CETP inhibitor such as, for example, torcetrapib or JTT-705 or those described in WO2006002342, WO2006010422, WO2006012093.

In one embodiment of the invention, the compound of the formula I is administered in combination with a bile acid absorption inhibitor (see, for example, U.S. Pat. Nos. 6,245,744, 6,221,897 or WO00/61568), such as, for example, HMR 1741 or those as described in DE 10 2005 033099.1 and DE 10 2005 033100.9.

In one embodiment of the invention, the compound of the formula I is administered in combination with a polymeric bile acid adsorbent such as, for example, cholestyramine or colesevelam.

In one embodiment of the invention, the compound of the formula I is administered in combination with an LDL receptor inducer (see U.S. Pat. No. 6,342,512), such as, for example, HMR1171, HMR1586 or those as described in WO2005097738.

In one embodiment, the compound of the formula I is administered in combination with Omacor® (omega-3 fatty acids; highly concentrated ethyl esters of eicosapentaenoic acid and of docosahexaenoic acid).

In one embodiment of the invention, the compound of the formula I is administered in combination with an ACAT inhibitor such as, for example, avasimibe or SMP-797.

In one embodiment of the invention, the compound of the formula I is administered in combination with an antioxidant such as, for example, OPC-14117, probucol, tocopherol, ascorbic acid, β-carotene or selenium.

In one embodiment of the invention, the compound of the formula I is administered in combination with a vitamin such as, for example, vitamin B6 or vitamin B12.

In one embodiment of the invention, the compound of the formula I is administered in combination with a lipoprotein lipase modulator such as, for example, ibrolipim (NO-1886).

In one embodiment of the invention, the compound of the formula I is administered in combination with an ATP citrate lyase inhibitor such as, for example, SB-204990.

In one embodiment of the invention, the compound of the formula I is administered in combination with a squalene synthetase inhibitor such as, for example, BMS-188494 or as described in WO2005077907.

In one embodiment of the invention, the compound of the formula I is administered in combination with a lipoprotein (a) antagonist such as, for example, gemcabene (CI-1027).

In one embodiment of the invention, the compound of the formula I is administered in combination with an agonist of GPR109A (HM74A receptor agonist) such as, for example, nicotinic acid or extended release niacin in conjunction with MK-0524A or those compounds described in WO2006045565, WO2006045564, WO2006069242.

In another embodiment of the invention, the compound of the formula I is administered in combination with an agonist of GPR116 as are described for example in WO2006067531, WO2006067532.

In one embodiment of the invention, the compound of the formula I is administered in combination with a lipase inhibitor such as, for example, orlistat or cetilistat (ATL-962).

In one embodiment of the invention, the compound of the formula I is administered in combination with insulin.

In one embodiment, the compound of the formula I is administered in combination with a sulfonylurea such as, for example, tolbutamide, glibenclamide, glipizide or glimepiride.

In one embodiment, the compound of the formula I is administered in combination with a substance which enhances insulin secretion, such as, for example, KCP-265 (WO2003097064).

In one embodiment, the compound of the formula I is administered in combination with agonists of the glucose-dependent insulinotropic receptor (GDIR) such as, for example, APD-668.

In one embodiment, the compound of the formula I is administered in combination with a biguanide such as, for example, metformin.

In yet another embodiment, the compound of the formula I is administered in combination with a meglitinide such as, for example, repaglinide or nateglinide.

In one embodiment, the compound of the formula I is administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, the compound of the formula I is administered in combination with an α-glucosidase inhibitor such as, for example, miglitol or acarbose.

In one embodiment, the compound of the formula I is administered in combination with an active ingredient which acts on the ATP-dependent potassium channel of the beta cells, such as, for example, tolbutamide, glibenclamide, glipizide, glimepiride or repaglinide.

In one embodiment, the compound of the formula I is administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment, the compound of the formula I is administered in combination with an inhibitor of glycogen phosphorylase, such as, for example, PSN-357 or FR-258900 or those as described in WO2003084922, WO2004007455, WO2005073229-31 or WO2005067932.

In one embodiment, the compound of the formula I is administered in combination with glucagon receptor antagonists such as, for example, A-770077, NNC-25-2504 or as described in WO2004100875 or WO2005065680.

In one embodiment, the compound of the formula I is administered in combination with activators of glucokinase, such as, for example, LY-2121260 (WO2004063179), PSN-105, PSN-110, GKA-50 or those as are described for example in WO2004072031, WO2004072066, WO2005080360, WO2005044801, WO2006016194, WO2006058923.

In one embodiment, the compound of the formula I is administered in combination with an inhibitor of gluconeogenesis, such as, for example, FR-225654.

In one embodiment, the compound of the formula I is administered in combination with inhibitors of fructose-1,6-bisphosphatase (FBPase), such as, for example, CS-917 (MB-06322) or MB-07803 or those described in WO2006023515.

In one embodiment, the compound of the formula I is administered in combination with modulators of glucose transporter 4 (GLUT4), such as, for example, KST-48 (D.-O. Lee et al.: Arzneim.-Forsch. Drug Res. 54 (12), 835 (2004)).

In one embodiment, the compound of the formula I is administered in combination with inhibitors of glutamine-fructose-6-phosphate amidotransferase (GFAT), as are described for example in WO2004101528.

In one embodiment, the compound of the formula I is administered in combination with inhibitors of dipeptidylpeptidase IV (DPP-IV), such as, for example, vildagliptin (LAF-237), sitagliptin (MK-0431), saxagliptin (BMS-477118), GSK-823093, PSN-9301, SYR-322, SYR-619, TA-6666, TS-021, GRC-8200, GW-825964X, KRP-104, DP-893 or as are described in WO2003074500, WO2003106456, WO200450658, WO2005058901, WO2005012312, WO2005/1012308, WO2006039325, WO2006058064, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment, the compound of the formula I is administered in combination with Januvia™, a fixed combination of sitagliptin phosphate with metformin hydrochloride.

In one embodiment, the compound of the formula I is administered in combination with inhibitors of 11-beta-hydroxysteroid dehydrogenase 1 (11β-HSD1), such as, for example, BVT-2733, JNJ-25918646, INCB-13739 or those as are described for example in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004058730, WO2004065351, WO2004089367, WO2004089380, WO2004089470-71, WO2004089896, WO2005016877, WO2005097759, WO2006010546, WO2006012227, WO2006012173, WO2006017542, WO2006034804, WO2006040329, WO2006051662, WO2006048750, WO2006049952, WO2006048331, WO2006050908, WO2006024627, WO2006040329, WO2006066109.

In one embodiment, the compound of the formula I is administered in combination with inhibitors of protein tyrosine phosphatase 1B (PTP1B), as are described for example in WO200119830-31, WO200117516, WO2004506446, WO2005012295, WO2005116003, PCT/

EP2005/005311, PCT/EP2005/005321, PCT/EP2005/007151, PCT/EP2005/01294 or DE 10 2004 060542.4.

In one embodiment, the compound of the formula I is administered in combination with modulators of the sodium-dependent glucose transporter 1 or 2 (SGLT1, SGLT2), such as, for example, KGA-2727, T-1095, SGL-0010, AVE 2268 and SAR 7226 or as are described for example in WO2004007517, WO200452903, WO200452902, PCT/EP2005/005959, WO2005085237, JP2004359630, WO2005121161, WO2006018150, WO2006035796, WO2006062224, WO2006058597 or by A. L. Handlon in Expert Opin. Ther. Patents (2005) 15(11), 1531-1540.

In one embodiment, the compound of the formula I is administered in combination with modulators of GPR40.

In one embodiment, the compound of the formula I is administered in combination with modulators of GPR119b as are described for example in WO2004041274.

In one embodiment, the compound of the formula I is administered in combination with modulators of GPR119 as are described for example in WO2005061489 (PSN-632408).

In one embodiment, the compound of the formula I is administered in combination with inhibitors of hormone-sensitive lipase (HSL) as described for example in WO2005073199.

In one embodiment, the compound of the formula I is administered in combination with inhibitors of acetyl-CoA carboxylase (ACC), such as, for example, those as described in WO199946262, WO200372197, WO2003072197, WO2005044814, WO2005108370, JP2006131559.

In one embodiment, the compound of the formula I is administered in combination with an inhibitor of phosphoenolpyruvate carboxykinase (PEPCK), such as, for example, those as described in WO2004074288.

In one embodiment, the compound of the formula I is administered in combination with an inhibitor of glycogen synthase kinase 3 beta (GSK-3 beta), as described for example in US2005222220, WO2005085230, PCT/EP2005/005346, WO2003078403, WO2004022544, WO2003106410, WO2005058908, US2005038023, WO2005009997, US2005026984, WO2005000836, WO2004106343, EP1460075, WO2004014910, WO2003076442, WO2005087727 or WO2004046117.

In one embodiment, the compound of the formula I is administered in combination with an inhibitor of protein kinase C beta (PKC beta), such as, for example, ruboxistaurin.

In one embodiment, the compound of the formula I is administered in combination with an endothelin A receptor antagonist such as, for example, avosentan (SPP-301).

In one embodiment, the compound of the formula I is administered in combination with inhibitors of "I-kappaB kinase" (IKK inhibitors), as are described for example in WO2001000610, WO2001030774, WO2004022553 or WO2005097129.

In one embodiment, the compound of the formula I is administered in combination with modulators of the glucocorticoid receptor, as are described for example in WO2005090336.

In a further embodiment, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists such as, for example, naphthalene-1-sulfonic acid {4-[(4-aminoquinazolin-2-ylamino)methyl] cyclohexylmethyl}amide hydrochloride (CGP 71683A);

NPY-5 receptor antagonists such as L-152804, S-2367 or as are described for example in WO2006001318;

Peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those as are described in WO2005080424;

CB1R (cannabinoid receptor 1) antagonists (such as, for example, rimonabant, SR147778 or those as are described for example in EP 0656354, WO 00/15609, WO 02/076949, WO2005080345, WO2005080328, WO2005080343, WO2005075450, WO2005080357, WO200170700, WO2003026647-48, WO200302776, WO2003040107, WO2003007887, WO2003027069, US6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509, WO2005077897, WO2006047516, WO2006060461, WO2006067428, WO2006067443); MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)) or LB53280, LB53279, LB53278 or THIQ, MB243, RY764, CHIR-785, PT-141 or those that are described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, EP1538159, WO2004072076, WO2004072077 or WO2006021655-57;

orexin receptor antagonists (e.g. 1-(2-methylbenzoxazol-6-yl)-3-[1,5]naphthyridin-4-ylurea hydrochloride (SB-334867-A) or those as are described for example in WO200196302, WO200185693, WO2004085403, WO2005075458 or WO2006067224);

histamine H3 receptor agonists (e.g. 3-cyclohexyl-1-(4,4-dimethyl-1,4,6,7-tetrahydroimidazo[4,5-c]pyridin-5-yl) propan-1-one oxalic acid salt (WO 00/63208) or those as are described in WO200064884, WO2005082893);

CRF antagonists (e.g. [2-methyl-9-(2,4,6-trimethylphenyl)-9H-1,3,9-triazafluoren-4-yl]dipropylamine (WO 00/66585));

CRF BP antagonists (e.g. urocortin);

urocortin agonists;

agonists of the beta-3 adrenoceptor such as, for example, 1-(4-chloro-3-methanesulfonylmethylphenyl)-2-[2-(2,3-dimethyl-1H-indol-6-yloxy)ethylamino]ethanol hydrochloride (WO 01/83451); or Solabegron (GW-427353) or N-5984 (KRP-204) or those described in JP2006111553;

MSH (melanocyte-stimulating hormone) agonists;

MCH (melanin-concentrating hormone) receptor antagonists (such as, for example, NBI-845, A-761, A-665798, A-798, ATC-0175, T-226296, T-71, GW-803430 or compounds such as are described in WO2003/15769, WO2005085200, WO2005019240, WO2004011438, WO2004012648, WO2003015769, WO2004072025, WO2005070898, WO2005070925, WO2004039780, WO2003033476, WO2002006245, WO2002089729, WO2002002744, WO2003004027, FR2868780, WO2006010446, WO2006038680, WO2006044293, WO2006044174);

CCK-A agonists (such as, for example, {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525), SR-146131 (WO 0244150) or SSR-125180 or those as are described in WO2005116034);

serotonin reuptake inhibitors (e.g. dexfenfluramine);

mixed sertoninergic and noradrenergic compounds (e.g. WO 00/71549);

5-HT receptor agonists, e.g. 1-(3-ethylbenzofuran-7-yl)piperazine oxalic acid salt (WO 01/09111);

5-HT2C receptor agonists (such as, for example, lorcaserin hydrochloride (APD-356), BVT-933 or those as are described in WO200077010, WO20077001-02, WO2005019180, WO2003064423, WO200242304 or WO2005082859);

5-HT6 receptor antagonists as are described for example in WO2005058858;

bombesin receptor agonists (BRS-3 agonists);

galanin receptor antagonists;

growth hormone (e.g. human growth hormone or AOD-9604);

growth hormone-releasing compounds (tertiary butyl 6-benzyloxy-1-(2-diisopropylaminoethylcarbamoyl)-3,4-dihydro-1H-isoquinoline-2-carboxylate (WO 01/85695));

growth hormone secretagogue receptor antagonists (ghrelin antagonists) such as, for example, A-778193 or those as are described in WO2005030734;

TRH agonists (see, for example, EP 0 462 884);

uncoupling protein 2 or 3 modulators;

leptin agonists (see, for example, Lee, Daniel W.; Leinung, Matthew C.;

Rozhayskaya-Arena, Marina; Grasso, Patricia. Leptin agonists as a potential approach to the treatment of obesity. Drugs of the Future (2001), 26(9), 873-881);

DA agonists (bromocriptine or Doprexin);

lipase/amylase inhibitors (for example WO 00/40569);

inhibitors of diacylglycerol O-acyltransferases (DGATs) such as, for example, BAY-74-4113 or as described for example in US2004/0224997, WO2004094618, WO200058491, WO2005044250, WO2005072740, JP2005206492, WO2005013907, WO2006004200, WO2006019020, WO2006064189;

inhibitors of fatty acid synthase (FAS) such as, for example, C75 or those as described in WO2004005277;

oxyntomodulin;

oleoyl-estrone or thyroid hormone receptor agonists such as, for example: KB-2115 or those as described in WO20058279, WO200172692, WO200194293, WO2003084915, WO2004018421 or WO2005092316.

In one embodiment, the further active ingredient is varenicline tartrate, a partial agonist of the alpha 4-beta 2 nicotinic acetylcholine receptor.

In one embodiment, the further active ingredient is trodusquemine.

In one embodiment, the further active ingredient is a modulator of the SIRT1 enzyme, a member of the human sirtuin enzyme family.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the further active ingredient is dexamphetamine or amphetamine.

In one embodiment, the further active ingredient is fenfluramine or dexfenfluramine.

In another embodiment, the further active ingredient is sibutramine.

In one embodiment, the further active ingredient is mazindole or phentermine.

In one embodiment, the compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Hochst, 65926 Frankfurt/Main). Combination with Caromax® is possible in one preparation or by separate administration of compounds of the formula I and Caromax®. Caromax® can in this connection also be administered in the form of food products such as, for example, in bakery products or muesli bars.

It will be understood that every suitable combination of the compounds of the invention with one or more of the aforementioned compounds and optionally one or more further pharmacologically active substances will be regarded as falling within the protection conferred by the present invention.

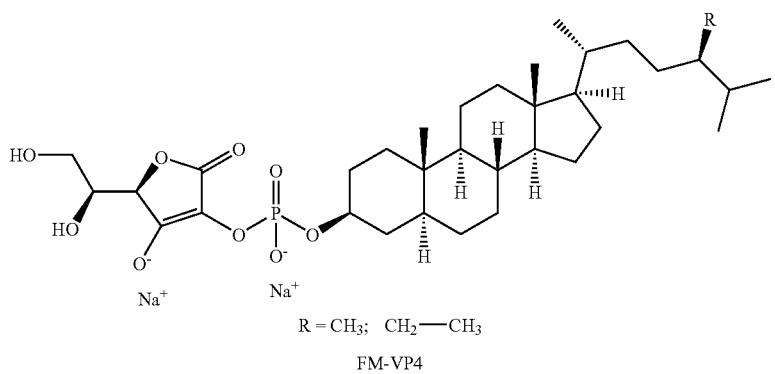

R = CH$_3$; CH$_2$—CH$_3$

FM-VP4

15
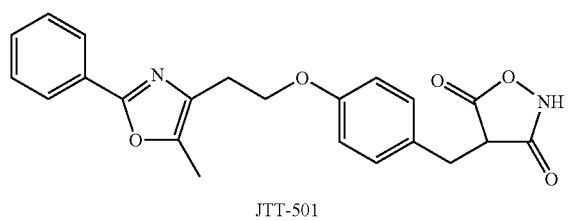
JTT-501
-continued
16
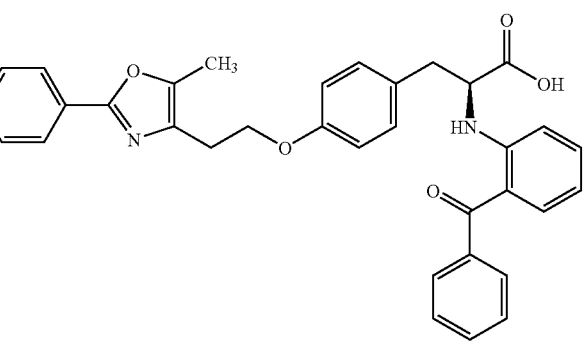
GI 262570
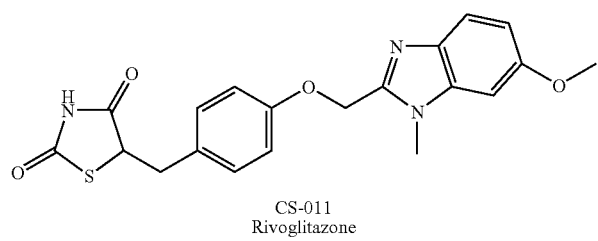
CS-011
Rivoglitazone
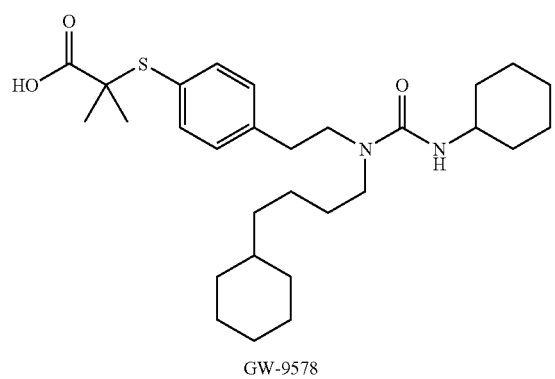
GW-9578
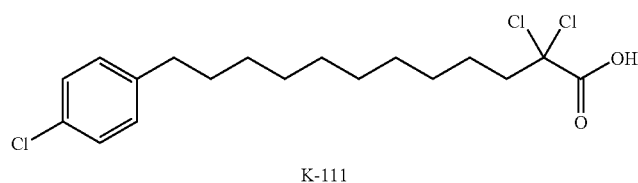
K-111
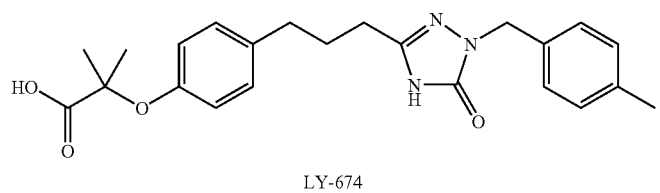
LY-674
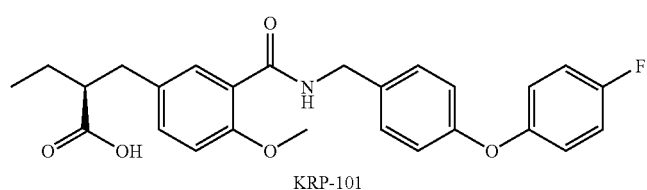
KRP-101
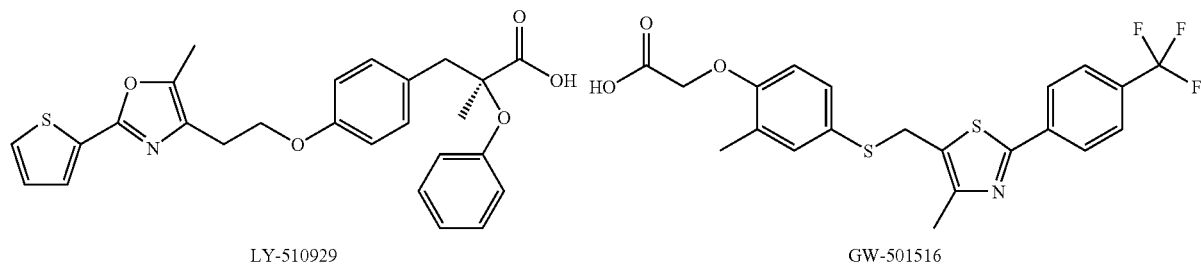
LY-510929          GW-501516

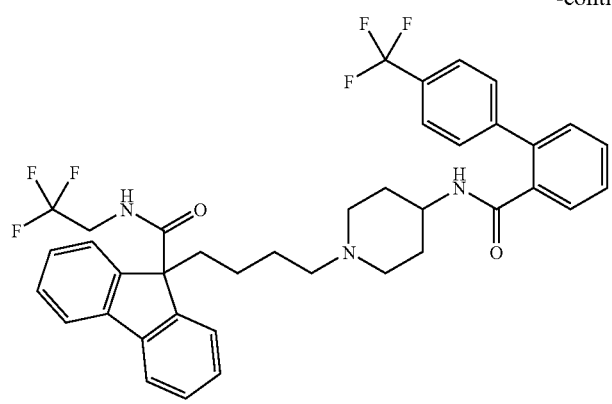
BMS-201038
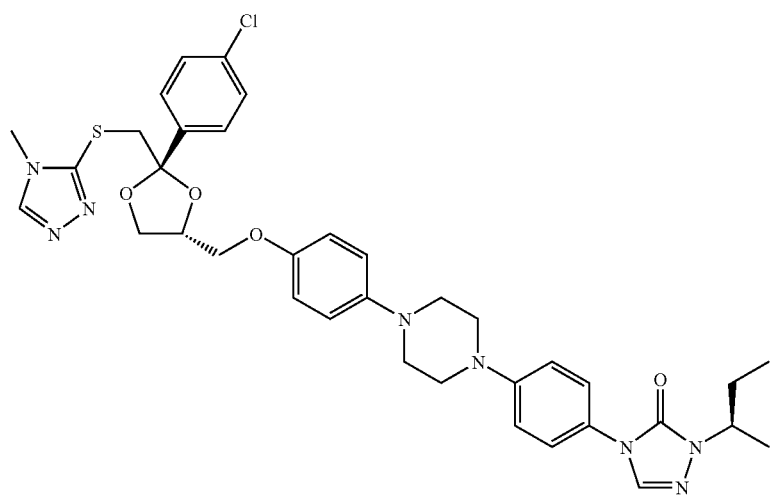
R-103757
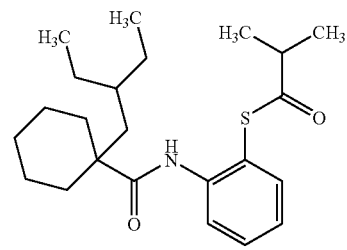
JTT-705
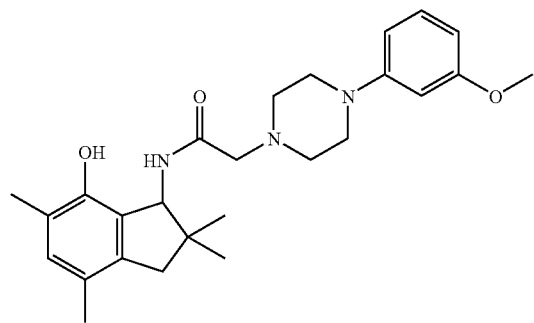
OPC-14117
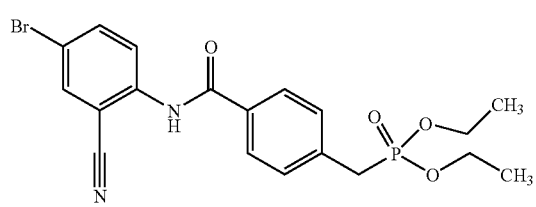
NO-1886
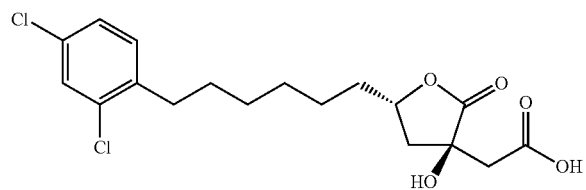
SB-204990

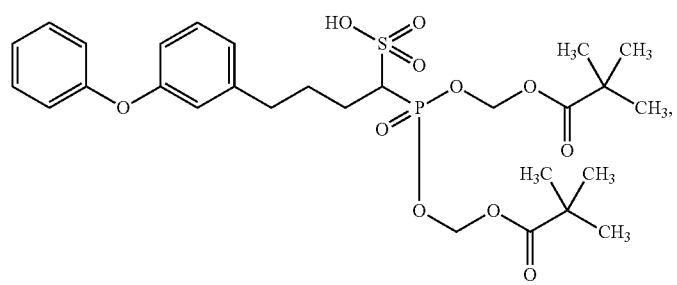
BMS-188494
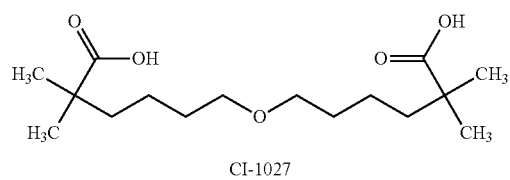
CI-1027
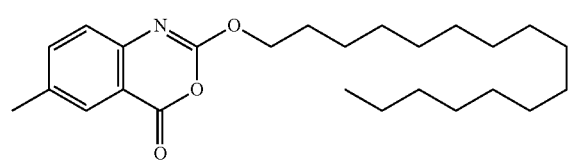
ATL-962
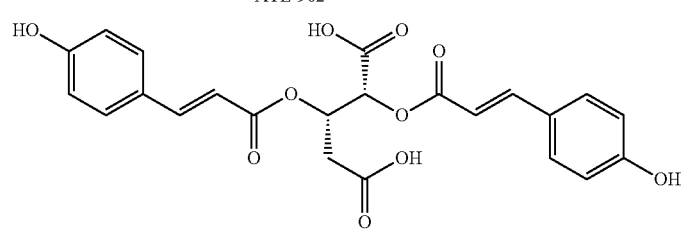
FR-258900
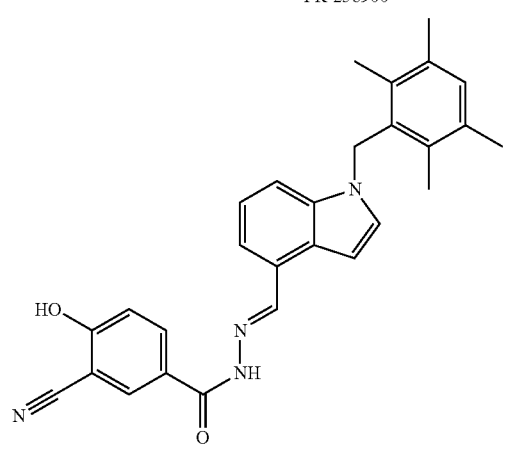
NNC-25-2504
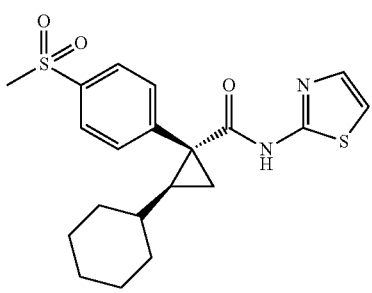
LY-2121260
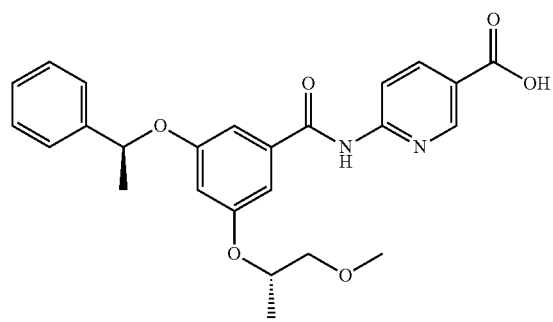
GKA-50
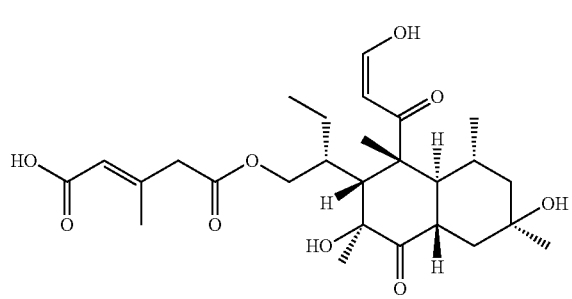
FR-225654

-continued
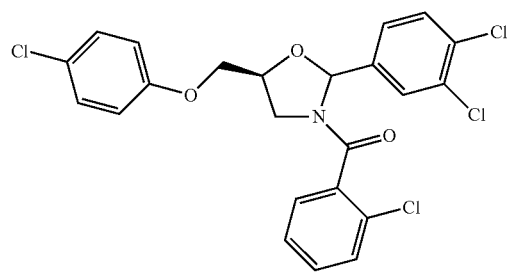
KST-48
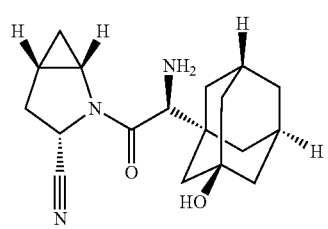
BMS-477118
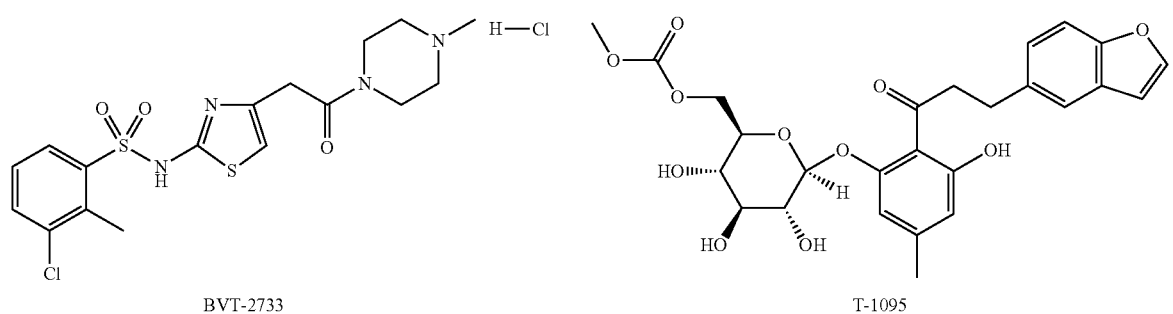
BVT-2733
T-1095
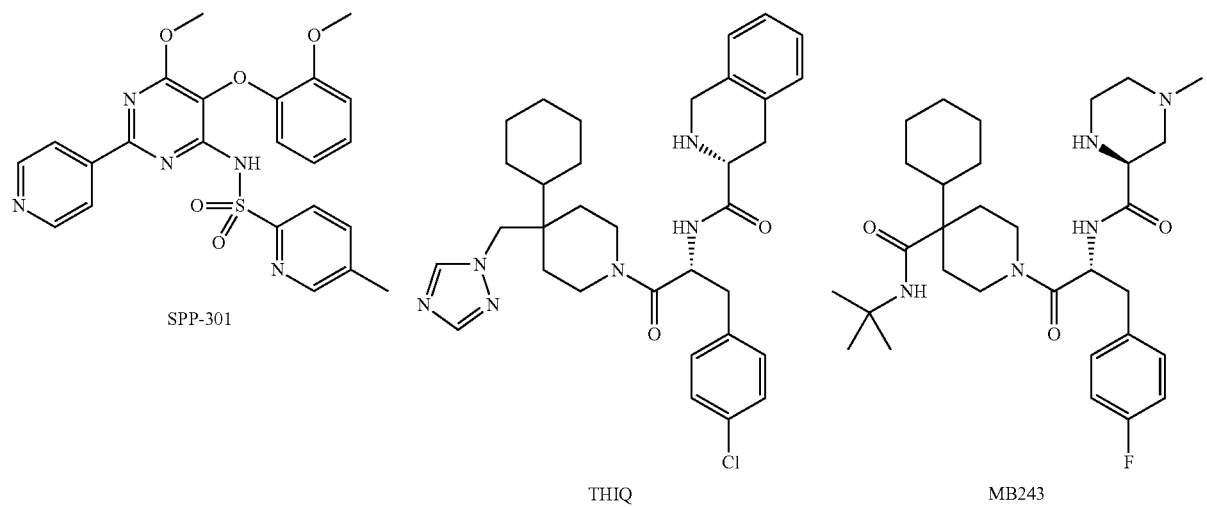
SPP-301
THIQ
MB243
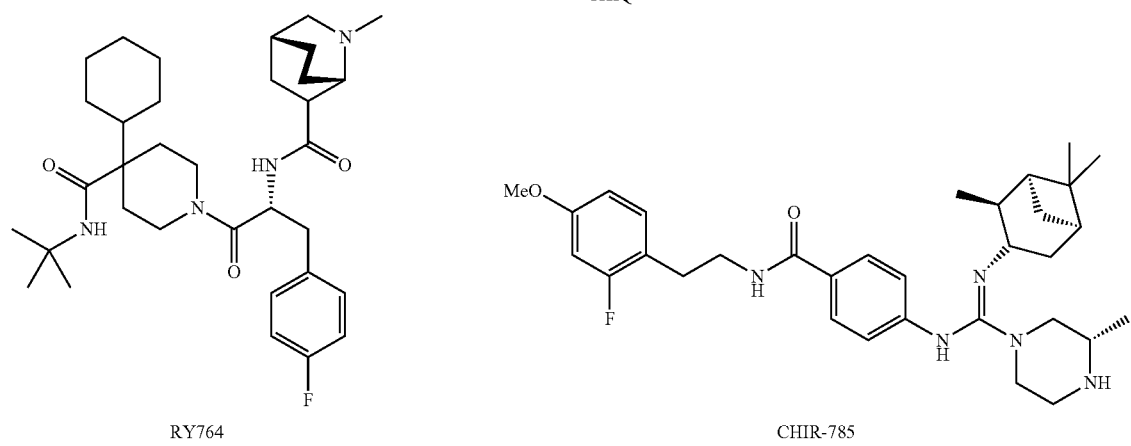
RY764
CHIR-785

-continued
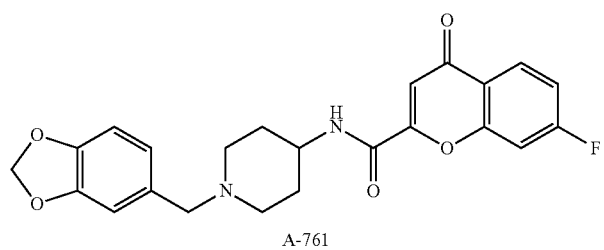
A-761
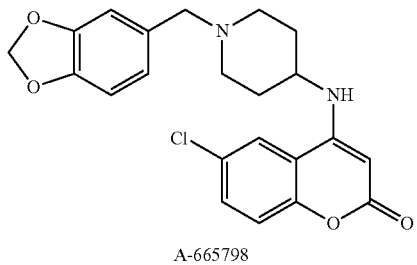
A-665798
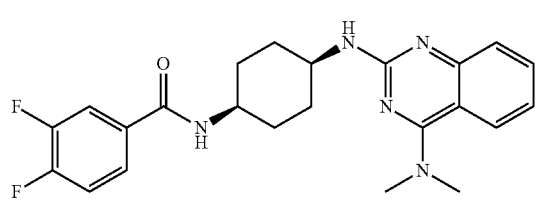
ATC-0175
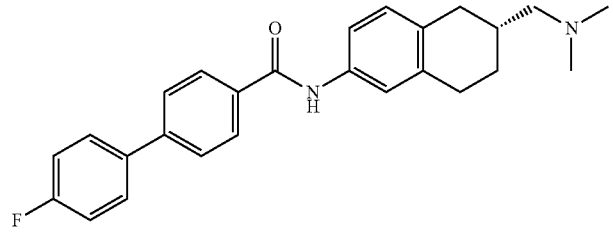
T-226296
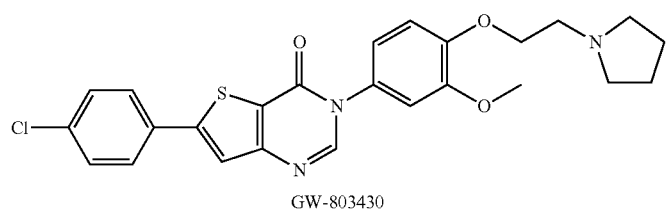
GW-803430
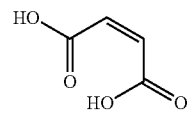
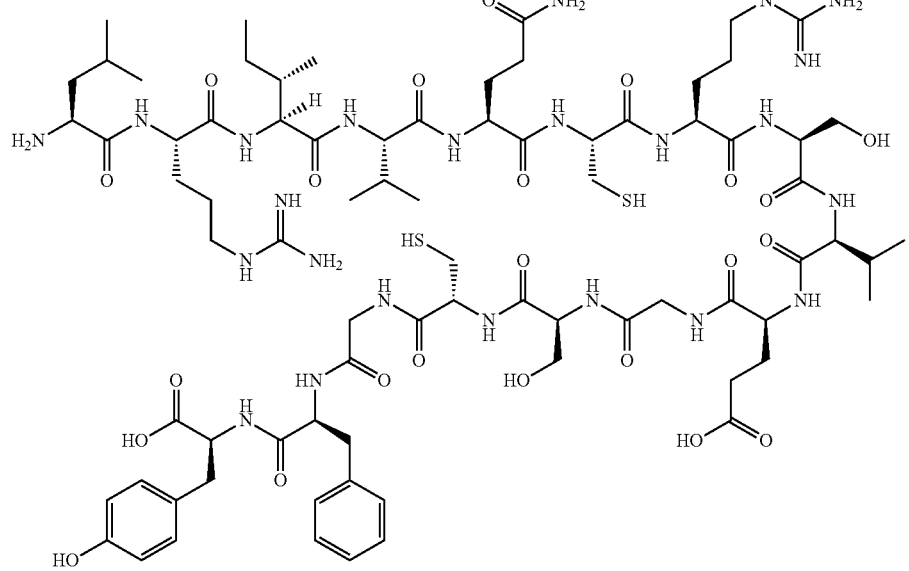
AOD-9604
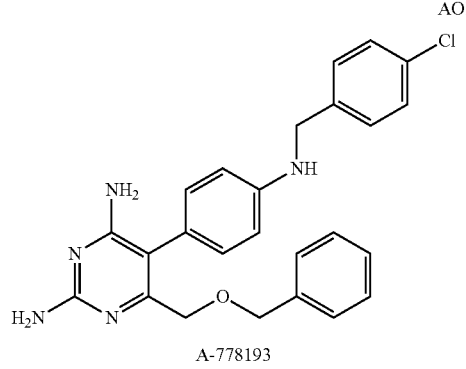
A-778193
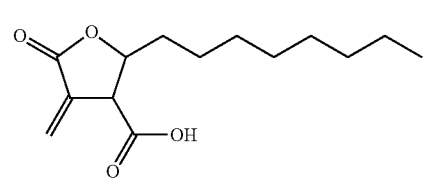
C75

-continued
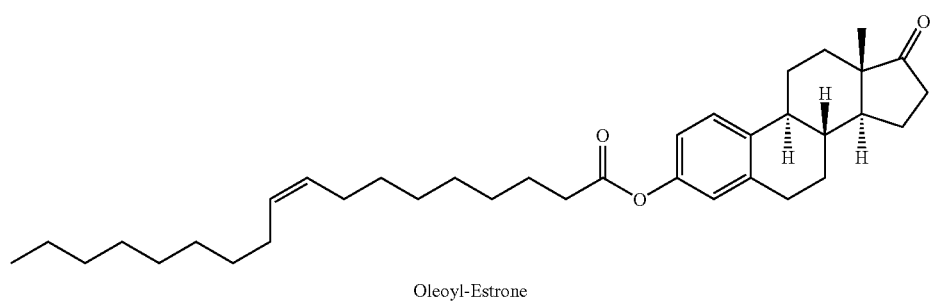
Oleoyl-Estrone
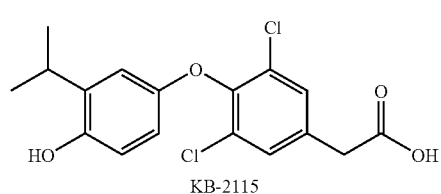
KB-2115
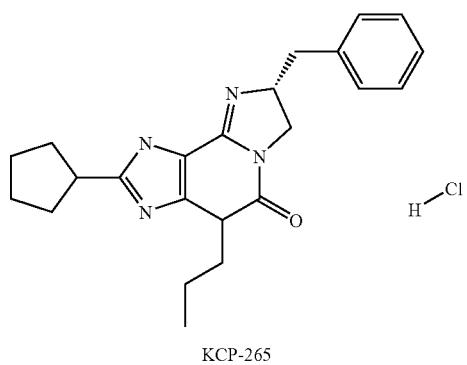
KCP-265
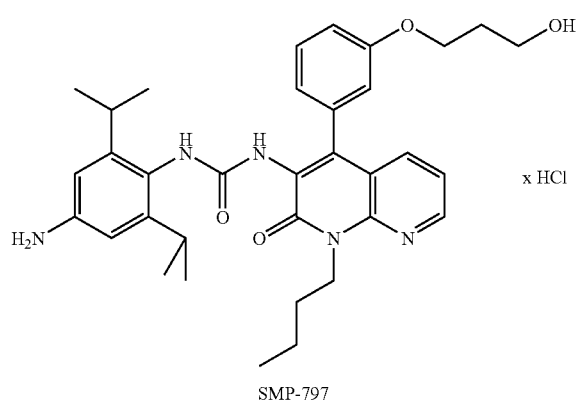
SMP-797
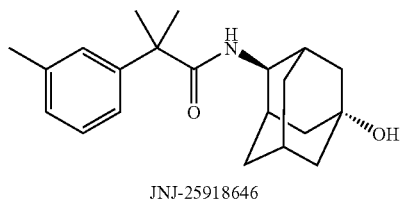
JNJ-25918646
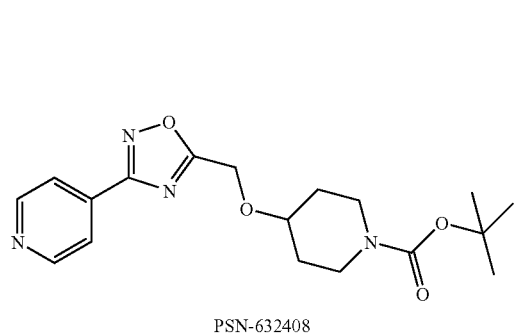
PSN-632408
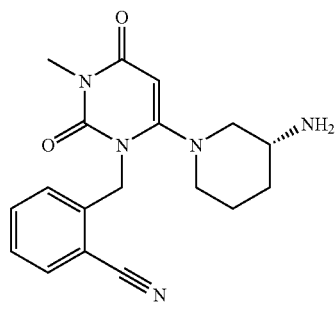
SYR-322
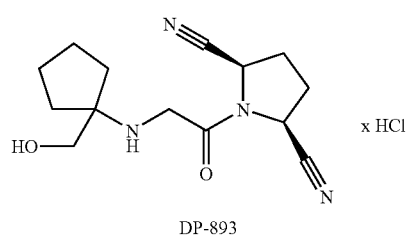
DP-893
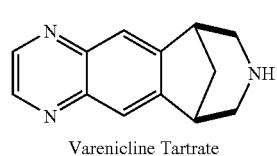
Varenicline Tartrate
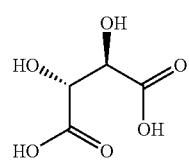

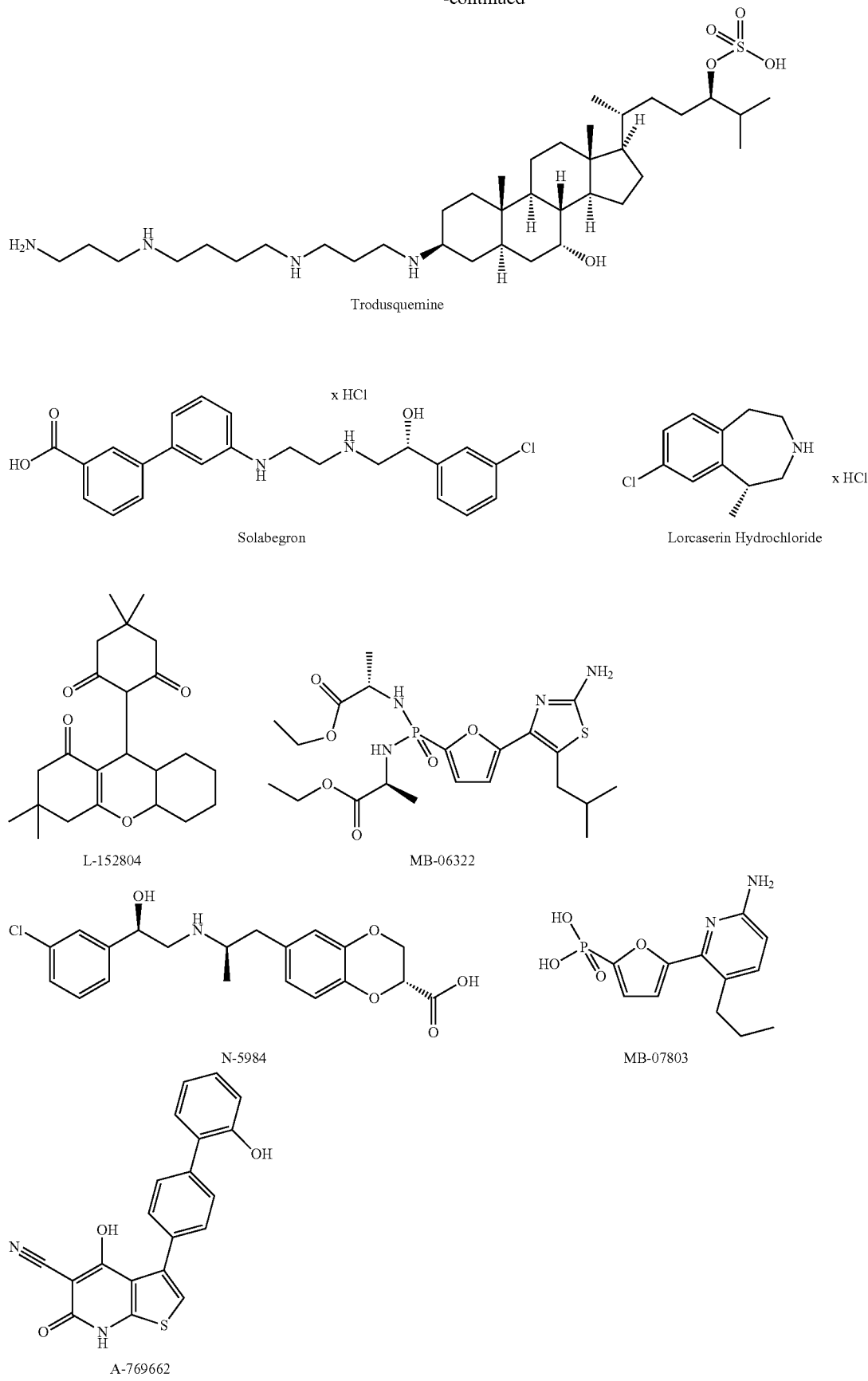

The examples detailed below serve to illustrate the invention without, however, restricting it.

TABLE 1

I

| Ex. | R1 | R2, R2' | R3, R3' | R4, R4' | R5, R5' | X |
|---|---|---|---|---|---|---|
| 1 | Et | OH, H | OH, H | F, H | CH$_2$OH, H | NH |
| 2 | Et | OH, H | OH, H | F, H | CH$_2$OSO$_2$OH, H | NH |
| 3 | Et | OH, H | OH, H | F, F | CH$_2$OH, H | NH |
| 4 | Et | OH, H | OH, H | F, F | CH$_2$OSO$_2$OH, H | NH |
| 5 | Et | OH, H | OH, H | F, H | CH$_2$SO$_2$OH, H | NH |

Et = ethyl

The activity of the compounds was assayed as follows:

Preparation and procedure for the in vitro IBAT inhibition assay:

1. Cloning of an Expression Vector for Human IBAT

The cDNA (complementary deoxyribonucleic acid) of human IBAT was cloned by standard methods of molecular biology as described for example in Molecular Cloning: A Laboratory Manual by Joseph Sambrook and David Russell, and introduced into the pcDNA1 vector from Invitrogen. The subsequent sequencing of the insert revealed complete identity with bases 599 to 1645 of the base sequence for human IBAT which was described by P. A. Dawson and is deposited in the Gen Bank sequence database (GenBank Accession Number: U10417). Bases 599 to 1645 correspond to the complete coding region of human IBAT.

2. Preparation of a Recombinant Cell Line with Constitutive Expression of Human IBAT The expression vector for human IBAT was introduced by stable transfection into CHO (chinese hamster ovary) cells. To select single cell clones, 400 μg/ml Geneticin was added to the cell culture medium (Ham's F12 medium supplemented with 10% fetal calf serum, 100 units/ml penicillin, 100 units/ml streptomycin). The functionality of the single cell clones resulting from the selection was assayed via their uptake activity for radiolabeled taurocholic acid ([$^3$H]-TCA). The cell clone with the highest uptake activity for [$^3$H]-TCA, referred to hereinafter as CHO-hIBAT, was selected for the further assays and further cultured in the presence of 400 μg/ml Geneticin.

3. Measurement of the Inhibitory Effect of the Compound of the Invention on the IBAT-Dependent Uptake of Taurocholic Acid into Cells CHO-hIBAT cells were seeded in a concentration of 40 000 cells per well in poly-D-lysine-coated 96-well plates in cell culture medium and cultured for 24 h. The cells were then washed once with sodium-free transport assay buffer (140 mM choline chloride, 2 mM potassium chloride, 1 mM magnesium chloride, 1 mM calcium chloride, 10 mM HEPES/Tris, pH 7.5) and subsequently incubated either with sodium-free transport assay buffer as negative control or with sodium-containing transport assay buffer (140 mM sodium chloride, 2 mM potassium chloride, 1 mM magnesium chloride, 1 mM calcium chloride, 10 mM HEPES/Tris, pH 7.5) as positive control at room temperature for 30 min. At the same time, the assay wells were also incubated in the presence of the compound to be investigated in varying concentration in sodium-containing transport assay buffer at room temperature for 30 min. The test substances were appropriately diluted in transport assay buffer (40 μl/well) starting from a 10 mM stock solution in dimethyl sulfoxide. The assay was then started by adding 10 μl/well of a mixture of radiolabeled taurocholic acid ([$^3$H]-TCA) and unlabeled taurocholic acid. The final concentration of taurocholic acid in the assay was 10 μM. After an incubation time of 60 min at room temperature, the reaction was stopped by adding 100 μl/well sodium-free transport assay buffer (4° C.), and each well was washed three times with sodium-free transport assay buffer. Finally, 100 μl of scintillation fluid were added to each well, and the radioactivity taken up into the cells was determined in a MicroBeta Scintillation Microplate Reader from Wallac.

The half-maximum inhibitory effect of the test compound (IC50 value, inhibitory concentration 50) was determined in the following way:

1. Determination of the value for 0% inhibition. This is the measurement in the absence of substance, measured in sodium-containing transport assay buffer.
2. Determination of the value for 100% inhibition. This is the measurement in the absence of substance, measured in sodium-free transport assay buffer.
3. Calculation of the percentage inhibitions of those measurements carried out in the presence of various concentrations of the compound to be investigated. It was then possible to find therefrom the concentration of the compound which reduces the uptake of taurocholic acid by 50% (IC50 value).

TABLE 2

Biological activity

| Ex. | IC-50 (human IBAT) μM |
|---|---|
| 1 | 0.0065 |
| 2 | 0.0039 |
| 3 | 0.0053 |
| 4 | 0.0036 |
| 5 | 0.0056 |

It can be inferred from the measured data that the compounds of the invention of the formula I are very suitable for the treatment of hyperlipidemia.

The use of the compounds of the formula I for the treatment or prevention of further diseases is likewise conceivable. Examples of such diseases are:

1. disorders of fatty acid metabolism and glucose utilization disorders
   disorders in which insulin resistance is involved
2. Diabetes mellitus, especially type 2 diabetes, including the prevention of the sequelae associated therewith.
   Particular aspects in this connection are
   hyperglycemia,
   improvement in insulin resistance,
   improvement in glucose tolerance,
   protection of the pancreatic β cells
   prevention of macro- and microvascular disorders 3. Dyslipidemias and their sequelae such as, for example, atherosclerosis, coronary heart disease, cerebrovascular disorders etc, especially those (but not restricted thereto) which are characterized by one or more of the following factors:
   high plasma triglyceride concentrations, high postprandial plasma triglyceride concentrations,
   low HDL cholesterol concentration
   low apoA lipoprotein concentrations
   high LDL cholesterol concentrations
   small dense LDL cholesterol particles
   high apoB lipoprotein concentrations
   desaturation index (e.g. ratio 18:1/18:0n-9, 16:1/16:0 n-7 or or 18:1n-9+16:1n-7/16:0 fatty acids)
4. Various other conditions which may be associated with the metabolic syndrome or syndrome X, such as:
   increased abdominal girth
   dyslipidemia (e.g. hypertriglyceridemia and/or low HDL)
   insulin resistance
   hypercoagulability
   hyperuricemia
   microalbuminemia
   thromboses, hypercoagulable and prothrombotic states (arterial and venous)
   high blood pressure
   heart failure such as, for example (but not restricted thereto), following myocardial infarction, hypertensive heart disease or cardiomyopathy
5. Hepatic disorders and conditions related thereto
   fatty liver
   hepatic steatosis
   non-alcoholic hepatitis
   non-alcoholic steatohepatitis (NASH)
   alcoholic hepatitis
   acute fatty liver
   fatty liver of pregnancy
   drug-induced hepatitis
   iron overload disorders
   hepatic fibrosis
   hepatic cirrhosis
   hepatoma
   viral hepatitis
6. Skin disorders and conditions and those associated with polyunsaturated fatty acids
   eczema
   acne
   psoriasis
   keloid scar formation or prevention
   other diseases related to mucous membrane fatty acid composition
7. Primary hypertriglyceridemia or secondary hypertriglyceridemias following
   familial histiocytic reticulosis
   lipoprotein lipase deficiency
   hyperlipoproteinemias
   apolipoprotein deficiency (e.g. apoCII or apoE deficiency)
8. Diseases or conditions related to neoplastic cellular proliferation
   benign or malignant tumors
   cancer
   neoplasia
   metastases
   carcinogenesis
9. Diseases or conditions related to neurological, psychiatric or immune disorders or conditions
10. Other diseases or conditions in which inflammatory reactions or cell differentiation may for example be involved are:
    atherosclerosis such as, for example (but not restricted thereto), coronary sclerosis including angina pectoris or myocardial infarction, stroke, ischemic stroke and transient ischemic attack (TIA)
    peripheral occlusive disease
    vascular restenosis or reocclusion
    chronic inflammatory bowel diseases such as, for example, Crohn's disease and ulcerative colitis
    pancreatitis
    sinusitis
    other inflammatory conditions
    retinopathy, ischemic retinopathy
    adipose cell tumors
    lipomatous carcinomas such as, for example, liposarcomas
    solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc
    acute and chronic myeloproliferative disorders and lymphomas
    angiogenesis
    neurodegenerative disorders
    Alzheimer's disease
    multiple sclerosis
    Parkinson's disease
    erythemato-squamous dermatoses such as, for example, psoriasis
    acne vulgaris
    other skin disorders and dermatological conditions which are modulated by PPAR
    eczemas and neurodermatitis
    dermatitis such as, for example, seborrheic dermatitis or photodermatitis
    keratitis and keratoses such as, for example, seborrheic keratoses, senile keratoses, actinic keratosis, photo-induced keratoses or keratosis follicularis
    keloids and keloid prophylaxis
    warts, including condylomata or condylomata acuminata
    human papilloma viral (HPV) infections such as, for example, venereal papillomata, viral warts such as, for example, molluscum contagiosum, leukoplakia
    papular dermatoses such as, for example, lichen planus
    skin cancer such as, for example, basal-cell carcinomas, melanomas or cutaneous T-cell lymphomas
    localized benign epidermal tumors such as, for example, keratoderma, epidermal naevi
    chilblains
    high blood pressure
    syndrome X
    polycystic ovary syndrome (PCOS)
    asthma
    cystic fibrosis
    osteoarthritis
    lupus erythematosus (LE) or inflammatory rheumatic disorders such as, for example, rheumatoid arthritis
    vasculitis
    wasting (cachexia)
    gout
    ischemia/reperfusion syndrome
    acute respiratory distress syndrome (ARDS)
    viral diseases and infections lypodystrophy and lipodystrophic conditions, also for treating adverse drug effects (e.g. after taking medicaments for treating HIV or tumors)

myopathies and lipid myopathies (such as carnitine palmitoyltransferase I or II deficiency)

The preparation of some examples is described in detail below; the other compounds of the formula I were obtained analogously:

EXPERIMENTAL SECTION

Example 1

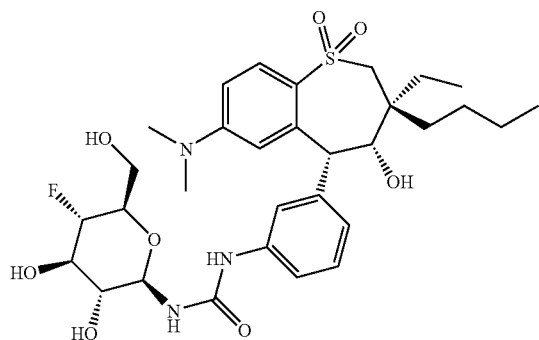

Ex.1

Synthesis of Compound 3:

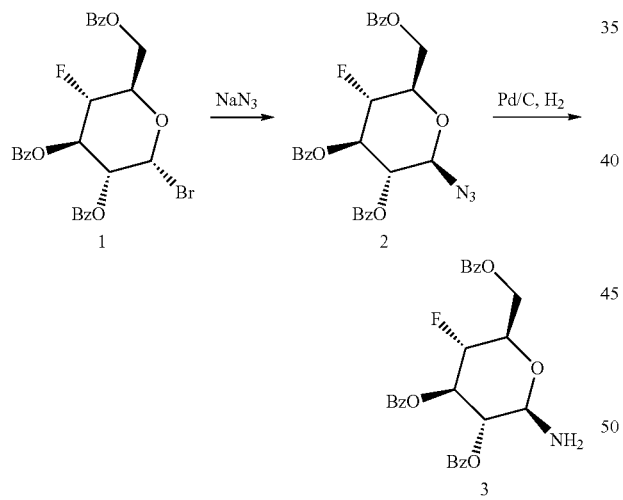

10.0 g (17.9 mmol) of bromide 1 (WO 2005121161) are dissolved in 100 ml of dimethylformamide. Addition of 2.2 g of sodium azide is followed by stirring at room temperature for one hour. The reaction solution is extracted with water and ethyl acetate, and the organic phase is washed twice more with saturated sodium chloride solution, filtered through a little silica gel and concentrated. 11.3 g of crude product 2 are obtained. This azide 2 is dissolved in 300 ml of ethyl acetate and 1.5 ml of triethylamine. Addition of 1 g of 10% palladium on activated carbon is followed by hydrogenation under a hydrogen pressure of 4 bar for 1 hour. The catalyst is removed on a little silica gel, and the silica gel is washed with ethyl acetate. The solution is concentrated and the residue is purified by flash chromatography. 7.0 g of colorless solid 3 (80% yield over 2 stages) are obtained. TLC (ethyl acetate). $R_f$=0.3. $C_{27}H_{24}NO_7$ (493.49). MS (M+H)$^+$=494.27.

Synthesis of Compound 4:

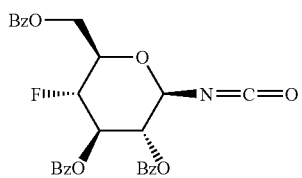

4

2.0 g (4.1 mmol) of amine derivative 3 are dissolved in 50 ml of methylene chloride. Addition of 30 ml of saturated aqueous sodium bicarbonate solution is followed by cooling to 0° C. and addition of 2 g (6.7 mmol) of triphosgene (Aldrich). The reaction is allowed to take place at room temperature for 60 minutes. The solution is then washed with saturated sodium bicarbonate solution, filtered through a little silica gel and concentrated, and 2.0 g of crude product isocyanate 4 are obtained as a colorless oil which is reacted further without further purification (isocyanate 4 decomposes during chromatography).

Synthesis of Example 1

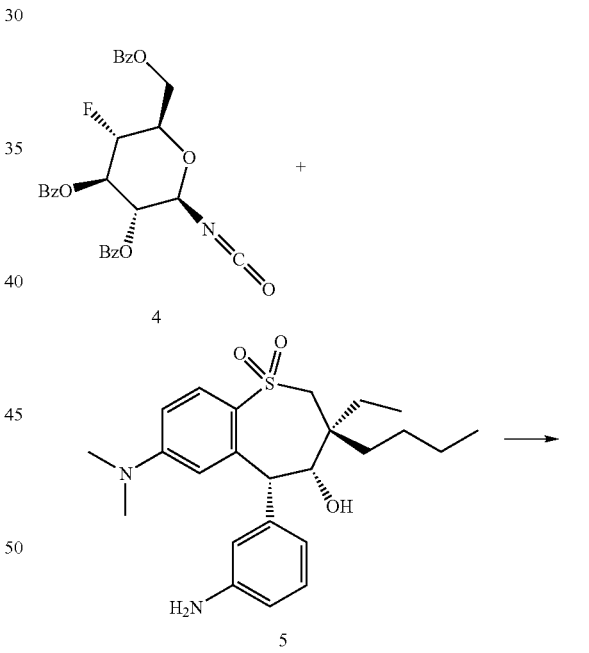

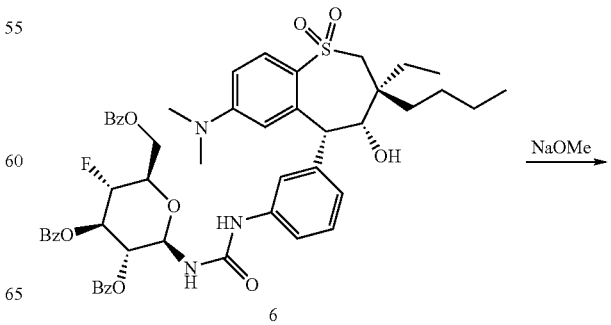

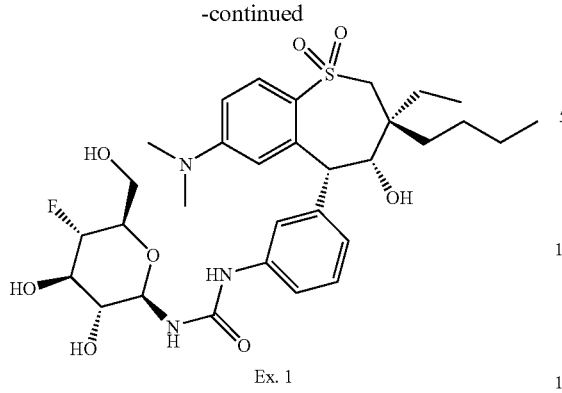

Ex. 1

Synthesis of Compound 6:

940 mg (2.2 mmol) of anilide 5 (U.S. Pat. No. 5,994,391) and 940 mg (1.8 mmol) of isocyanate 4 are dissolved in 50 ml of methylene chloride at room temperature. After one hour at room temperature, the mixture is concentrated to result in 1.9 g of crude product 6 as a colorless solid. TLC (n-heptane/ethyl acetate 1:1). $R_f$=0.3.

Synthesis of Example 1

1.9 g of crude product 6 are dissolved in 20 ml of methanol, and 0.5 ml of 1 M sodium methanolate/methanol solution is added. After 30 minutes, the reaction solution is neutralized with 1 ml of 0.5 M HCL/methanol solution and concentrated. The residue is purified by flash chromatography. Yield 870 mg (76% over 2 stages) of Ex. 1 as colorless solid. TLC (methylene chloride/methanol/conc. ammonia 30/5/1). $R_f$=0.5. $C_{31}H_{44}FN_3O_8S$ (637.77). MS $(M+H)^+$=638.38.

Example 2

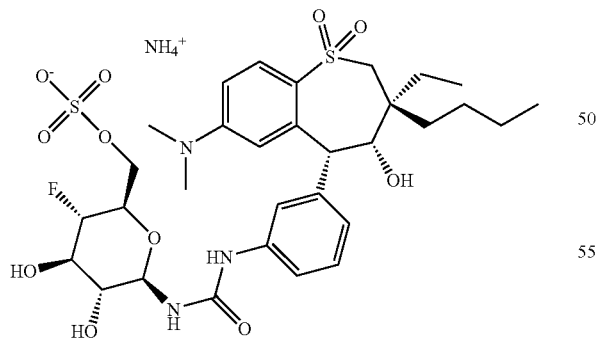

Ex. 2

250.0 mg (0.39 mmol) of Example 1 are dissolved in 5 ml of pyridine and, after addition of 100 mg of pyridine-sulfur trioxide complex, stirred at 60° C. for 30 minutes. Addition of 10 ml of methanol is followed by concentration in a rotary evaporator. The residue is evaporated once again with 10 ml of methanol and then purified by flash chromatography. Yield 210 mg (75%) of Ex. 2 as ammonium salt. TLC (methylene chloride/methanol/conc. ammonia 30/5/1). $R_f$=0.3. $C_{31}H_{44}FN_3O_{11}S_2 \times NH_3$ (734.87). MS $(M+H)^+$=718.39

Synthesis of Isocyanate 9

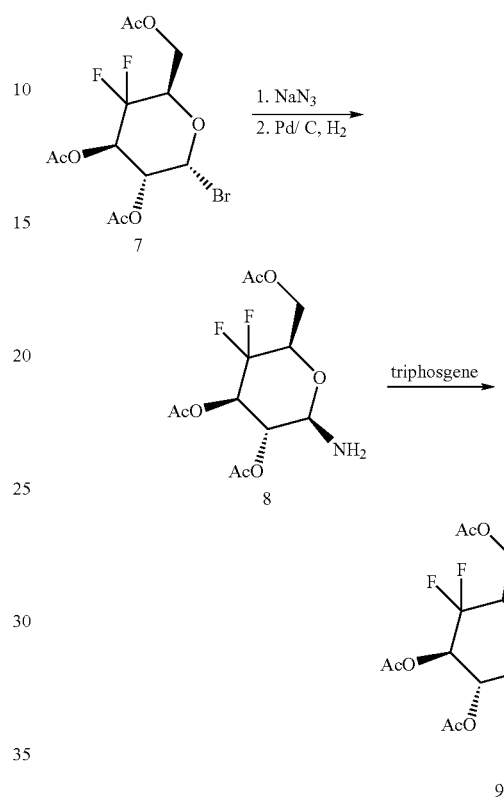

Isocyanate 9 is prepared as crude product starting from bromide 7 (WO 2004 052903) via the amine 8 in analogy to the synthesis of isocyanate 4.

Example 3

Ex. 3

Example 3 is prepared starting from 60 mg of isocyanate 9 and 184 mg of aniline 5 in analogy to the synthesis of Example 1, and 50 mg (45% yield over 2 stages) of Ex. 3 are obtained as a colorless solid. TLC (methylene chloride/ methanol/conc. ammonia 30/5/1). $R_f$=0.5. $C_{31}H_{43}F_2N_3O_8S$ (655.76). MS (M+H)$^+$=656.32.

Example 4

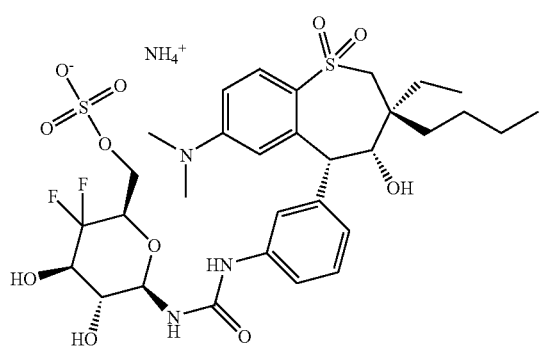

Ex. 4

Example 4 is prepared starting from 30 mg of Example 3 in analogy to the described synthesis of Example 2, and 17 mg (55%) of ammonium salt of Example 4 are obtained. TLC (methylene chloride/methanol/conc. ammonia 30/5/1). $R_f$=0.3. $C_{31}H_{43}F_2N_3O_{11}S_2 \times NH_3$ (752.86). MS (M+H)$^-$= 734.39.

Example 5

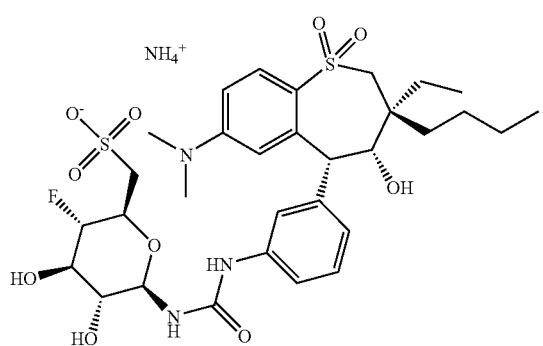

Ex. 5

Synthesis of Tosylate 10:

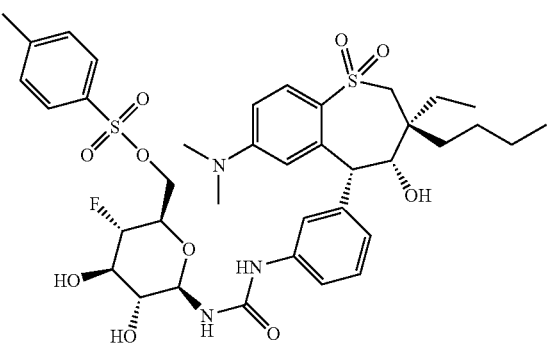

10

670 mg (1.1 mmol) of Example 1 are dissolved in 5 ml of pyridine and, at room temperature, 460 mg (2.4 mmol) of p-tosly chloride are added. After 1 hour at room temperature, 20 ml of methanol are added, and the solvent is distilled off. The residue is purified by flash chromatography. Yield 800 mg (96%) of tosylate 10 as colorless solid. TLC (methylene chloride/methanol/conc. ammonia 30/5/1). $R_f$=0.7. $C_{38}H_{50}FN_3O_{10}S_2$ (791.97). MS (M+H)$^+$=792.34.

Synthesis of Compound 11:

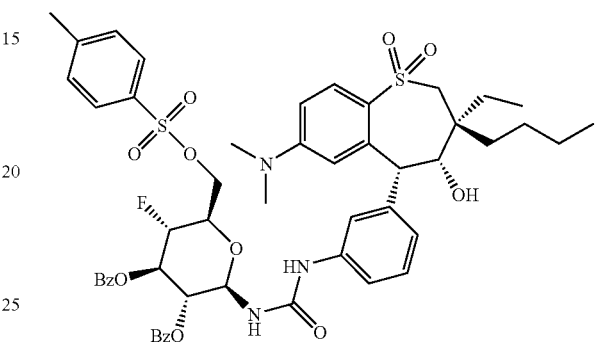

11

800 mg (1.0 mmol) of tosylate 10 are dissolved in 15 ml of pyridine and, at 0° C., 0.32 ml of benzoyl chloride is added. The cooling is removed and, after 1 hour at room temperature, 20 ml of methanol are added and the solvent is distilled off. The residue is purified by flash chromatography. Yield 800 mg (80%) of compound 11 as colorless solid. TLC (n-heptane/ethyl acetate ½). $R_f$=0.5. $C_{52}H_{58}FN_3O_{12}S_2$ (1000.18). MS (M+H)$^+$=1000.32.

Synthesis of Compound 12:

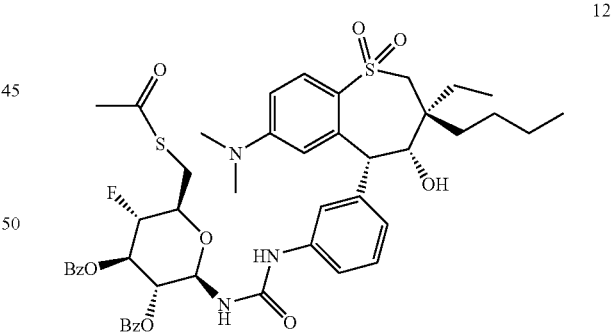

12

800 mg (0.8 mmol) of tosylate 11 are dissolved in 10 ml of dimethylformamide. Addition of 550 mg of potassium thioacetate is followed by stirring at room temperature for 2 hours. The reaction solution is extracted with water and ethyl acetate, and the organic phase is washed twice more with saturated sodium chloride solution, filtered through a little silica gel and concentrated. The residue is purified by flash chromatography (n-heptane/ethyl acetate), and 560 mg (77% yield) of thioacetate 12 are obtained as a colorless solid. TLC (n-heptane/ethyl acetate 1:2). $R_f$=0.5. $C_{47}H_{54}FN_3O_{10}S_2$ (904.09). MS (M+H)$^+$=904.29.

Synthesis of Compound 13:

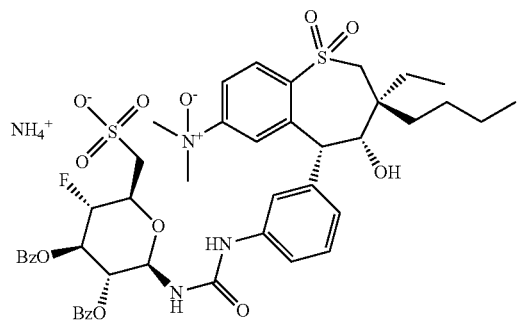

Preparation of the Oxidizing Solution A:
1.5 ml of 30% strength aqueous hydrogen peroxide solution are dissolved in 13.5 ml of formic acid and left to stand for 1 hour. This solution can be stored in a refrigerator for several weeks.

560 mg (0.62 mmol) of thioacetate 12 are dissolved in 14.5 ml of oxidizing solution A. After 2 hours at room temperature, the mixture is diluted with ethyl acetate and saturated sodium chloride solution. The aqueous phase is extracted twice more with ethyl acetate, and the collected organic phases are dried over magnesium sulfate, filtered and concentrated. The residue is purified by flash chromatography. Yield 446 mg (78%) of sulfonate 13 as yellowish ammonium salt. TLC (methylene chloride/methanol/conc. ammonia 30/5/1). $R_f$=0.5. $C_{45}H_{52}FN_3O_{13}S_2\times NH_3$ (943.09). MS (M+H)$^+$=926.23.

Synthesis of Compound 14:

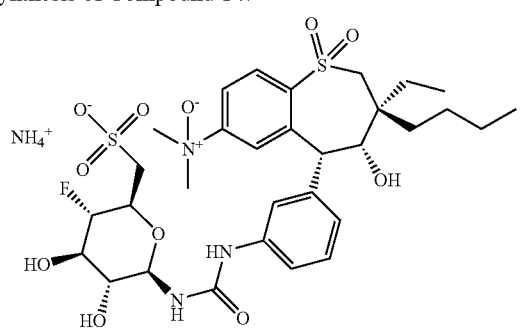

446 mg (0.47 mmol) of ammonium salt 13 are dissolved in 5 ml of methanol, and 0.5 ml of 1 M sodium methanolate/methanol solution is added. After 30 minutes, the reaction solution is neutralized with 1 ml of 0.5 M HCL/methanol solution and concentrated. The residue is purified by flash chromatography. Yield 293 mg (84%) of N-oxide 14 as colorless solid. TLC (methylene chloride/methanol/conc. ammonia 30/15/5). $R_f$=0.2. $C_{31}H_{44}FN_3O_{11}S_2\times NH_3$(734.87). MS (M+H)$^+$=718.24.

Example 5

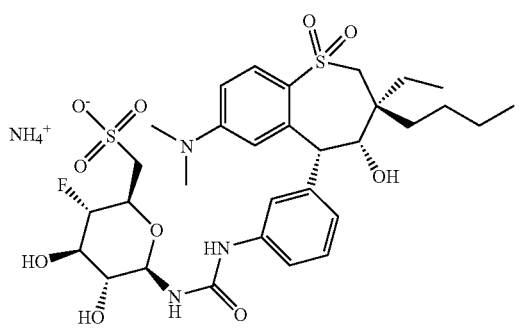

287 mg (0.39 mmol) of N-oxide 14 are dissolved in 10 ml of methanol and 2 ml of 0.5 M HCl/methanol. Addition of 200 mg of 10% palladium on activated carbon is followed by hydrogenation under a hydrogen pressure of 6 bar for 1 hour. The solution is concentrated and the residue is purified by flash chromatography. Yield 205 mg (73%) of sulfonate of Example 5 as colorless solid. TLC (methylene chloride/methanol/conc. ammonia 30/15/5). $R_f$=0.6. $C_{31}H_{44}FN_3O_{10}S_2\times NH_3$(718.87). MS (M+H)$^+$=702.19.

The invention claimed is:

1. A compound of the formula I

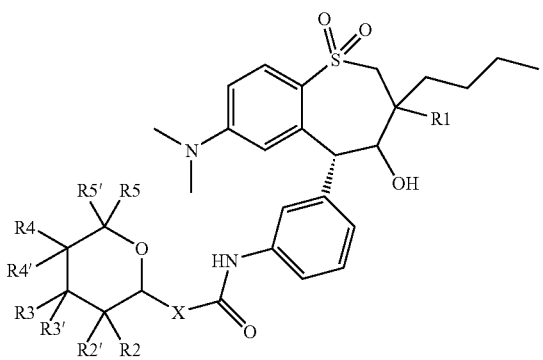

wherein

X is O, NH, CH$_2$ or a bond;

R1 is (C$_1$-C$_6$)-alkyl;

R2, R2', R3, R3', R4, R4', R5, R5' are, independently of one another, H, F, Cl, Br, I, OH, —(CH$_2$)—OH, CH$_2$F, CHF$_2$, CF$_3$, NO$_2$, N$_3$, CN, S(O)$_p$—R6, (C$_1$-C$_6$)-alkylene-S(O)$_p$—R6, COOH, COO(C$_1$-C$_6$)alkyl, CONH$_2$, CONH(C$_1$-C$_6$)alkyl, CON[(C$_1$-C$_6$)alkyl]$_2$, (C$_1$-C$_6$)-alkyl, (C$_2$-C$_6$)-alkenyl, (C$_2$-C$_6$)-alkynyl, O—(C$_1$-C$_6$)-alkyl, where one, more than one, or all hydrogen(s) in the alkyl radicals may be replaced by fluorine;

phenyl, —(CH$_2$)-phenyl, —(CH$_2$)$_n$-phenyl, O-phenyl, O—(CH$_2$)$_m$-phenyl, —(CH$_2$)—O—(CH$_2$)$_m$-phenyl, where the phenyl ring may be substituted one to 3 times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl or CONH$_2$;

wherein at least one of the radicals R2, R2', R3, R3', R4, R4' has the meaning of fluorine or R5, R5' has the meaning of CH$_2$F, CHF$_2$ or CF$_3$;

R6 is H, OH, (C$_1$-C$_6$)-alkyl, NH$_2$, NH(C$_1$-C$_6$)-alkyl or N((C$_1$-C$_6$)-alkyl)$_2$;

n is 2, 3, 4, 5 or 6;

m is 1, 2, 3, 4, 5 or 6;

p is 0, 1 or 2;

or a pharmaceutically acceptable salt thereof.

2. The compound of claim 1 wherein

X is NH;

R1 is $(C_1\text{-}C_6)$-alkyl;

R2, R2', R3, R3', R4, R4', R5, R5' are, independently of one another, H, F, Cl, Br, I, OH, —(CH$_2$)—OH, CH$_2$F, CHF$_2$, CF$_3$, NO$_2$, N$_3$, CN, S(O)$_p$—R6, $(C_1\text{-}C_6)$-alkylene-S(O)$_p$—R6, COOH, COO$(C_1\text{-}C_6)$alkyl, CONH$_2$, CONH$(C_1\text{-}C_6)$alkyl, CON$[(C_1\text{-}C_6)$alkyl$]_2$, $(C_1\text{-}C_6)$-alkyl, $(C_2\text{-}C_6)$-alkenyl, $(C_2\text{-}C_6)$-alkynyl, O—$(C_1\text{-}C_6)$-alkyl, where one, more than one, or all hydrogen(s) in the alkyl radicals may be replaced by fluorine;

phenyl, —(CH$_2$)-phenyl, —(CH$_2$)$_n$-phenyl, O-phenyl, O—(CH$_2$)—O—(CH$_2$)$_m$-phenyl, where the phenyl ring may be substituted one to 3 times by F, Cl, Br, I, OH, CF$_3$, NO$_2$, CN, OCF$_3$, O—$(C_1\text{-}C_6)$-alkyl, $(C_1\text{-}C_6)$-alkyl, NH$_2$, NH$(C_1\text{-}C_6)$-alkyl, N$((C_1\text{-}C_6)$-alkyl$)_2$, SO$_2$—CH$_3$, COOH, COO—$(C_1\text{-}C_6)$-alkyl or CONH$_2$;

wherein at least one of the radicals R2, R2', R3, R3', R4, R4' has the meaning of fluorine or R5, R5' has the meaning of CH$_2$F, CHF$_2$ or CF$_3$;

R6 is H, OH, $(C_1\text{-}C_6)$-alkyl, NH$_2$, NH$(C_1\text{-}C_6)$-alkyl or N$((C_1\text{-}C_6)$-alkyl$)_2$;

n is 2, 3, 4, 5 or 6;

m is 1, 2, 3, 4, 5 or 6;

p is 0, 1 or 2;

or a pharmaceutically acceptable salt thereof.

3. The compound of claim 2 wherein

X is NH;

R1 is $(C_1\text{-}C_6)$-alkyl;

R4 is F;

R4' is H or F;

R2, R2', R3, R3', R5, R5' are, independently of one another, H, F, Cl, Br, I, OH, —(CH$_2$)—OH, CH$_2$F, CHF$_2$, CF$_3$, NO$_2$, N$_3$, CN, S(O)$_p$—R6, $(C_1\text{-}C_6)$-alkylene-S(O)$_p$—R6, COOH, COO$(C_1\text{-}C_6)$alkyl, CONH$_2$, CONH$(C_1\text{-}C_6)$alkyl, CON$[(C_1\text{-}C_6)$alkyl$]_2$, $(C_1\text{-}C_6)$-alkyl, $(C_2\text{-}C_6)$-alkenyl, $(C_2\text{-}C_6)$-alkynyl, O—$(C_1\text{-}C_6)$-alkyl, where one, more than one, or all hydrogen(s) in the alkyl radicals may be replaced by fluorine;

phenyl, —(CH$_2$)-phenyl, —(CH$_2$)$_n$-phenyl, O-phenyl, O—(CH$_2$)$_m$-phenyl, —(CH$_2$)—O—(CH$_2$)$_m$-phenyl, where the phenyl ring may be substituted one to 3 times by F, Cl, Br, I, OH, CF$_3$, NO$_2$, CN, OCF$_3$, O—$(C_1\text{-}C_6)$-alkyl, $(C_1\text{-}C_6)$-alkyl, NH$_2$, NH$(C_1\text{-}C_6)$-alkyl, N$((C_1\text{-}C_6)$-alkyl$)_2$, SO$_2$—CH$_3$, COOH, COO—$(C_1\text{-}C_6)$-alkyl or CONH$_2$;

R6 is H, OH, $(C_1\text{-}C_6)$-alkyl, NH$_2$, NH$(C_1\text{-}C_6)$-alkyl or N$((C_1\text{-}C_6)$-alkyl$)_2$;

n is 2, 3, 4, 5 or 6;

m is 1, 2, 3, 4, 5 or 6;

p is 0, 1 or 2;

or a pharmaceutically acceptable salt thereof.

4. The compound of claim 1 wherein

X is O, NH, CH$_2$ or a bond;

R1 is $(C_1\text{-}C_6)$-alkyl;

R2, R2', R3, R3', R4, R4' are, independently of one another, H, F, Cl, Br, I, OH, —(CH$_2$)—OH, CH$_2$F, CHF$_2$, CF$_3$, NO$_2$, N$_3$, CN, S(O)$_p$—R6, $(C_1\text{-}C_6)$-alkylene-S(O)$_p$—R$_6$, COOH, COO$(C_1\text{-}C_6)$alkyl, CONH$_2$, CONH$(C_1\text{-}C_6)$alkyl, CON$[(C_1\text{-}C_6)$alkyl$]_2$, $(C_1\text{-}C_6)$-alkyl, $(C_2\text{-}C_6)$-alkenyl, $(C_2\text{-}C_6)$-alkynyl, O—$(C_1\text{-}C_6)$-alkyl, where one, more than one, or all hydrogen(s) in the alkyl radicals may be replaced by fluorine;

phenyl, —(CH$_2$)-phenyl, —(CH$_2$)$_n$-phenyl, O-phenyl, O—(CH$_2$)$_m$-phenyl, —(CH$_2$)—O—(CH$_2$)$_m$-phenyl, where the phenyl ring may be substituted one to 3 times by F, Cl, Br, I, OH, CF$_3$, NO$_2$, CN, OCF$_3$, O—$(C_1\text{-}C_6)$-alkyl, $(C_1\text{-}C_6)$-alkyl, NH$_2$, NH$(C_1\text{-}C_6)$-alkyl, N$((C_1\text{-}C_6)$-alkyl$)_2$, SO$_2$—CH$_3$, COOH, COO—$(C_1\text{-}C_6)$-alkyl or CONH$_2$;

R5, R5' are, independently of one another, H, —(CH$_2$)—OH, CH$_2$F, CHF$_2$, CF$_3$, S(O)$_p$—R6, $(C_1\text{-}C_6)$-alkylene-S(O)$_p$—R6, COOH, COO$(C_1\text{-}C_6)$alkyl, CONH$_2$, CONH$(C_1\text{-}C_6)$alkyl, CON$[(C_1\text{-}C_6)$alkyl$]$, $(C_1\text{-}C_6)$-alkyl,$(C_2\text{-}C_6)$-alkenyl, $(C_2\text{-}C_6)$-alkynyl, O—$(C_1\text{-}C_6)$-alkyl, where one, more than one, or all hydrogen(s) in the alkyl radicals may be replaced by fluorine;

phenyl, —(CH$_2$)-phenyl, —(CH$_2$)$_n$-phenyl, O-phenyl, O—(CH$_2$)$_m$-phenyl, —(CH$_2$)—O—(CH$_2$)$_m$-phenyl, where the phenyl ring may be substituted one to 3 times by F, Cl, Br, I, OH, CF$_3$, NO$_2$, CN, OCF$_3$, O—$(C_1\text{-}C_6)$-alkyl, $(C_1\text{-}C_6)$-alkyl, NH$_2$, NH$(C_1\text{-}C_6)$-alkyl, N$((C_1\text{-}C_6)$-alkyl$)_2$, SO$_2$—CH$_3$, COOH, COO—$(C_1\text{-}C_6)$-alkyl or CONH$_2$;

wherein at least one of the radicals R2, R2', R3, R3', R4, R4' has the meaning of fluorine or R5, R5' has the meaning of CH$_2$F, CHF$_2$ or CF$_3$;

R6 is H, OH, $(C_1\text{-}C_6)$-alkyl, NH$_2$, NH$(C_1\text{-}C_6)$-alkyl or N$((C_1\text{-}c_6)$-alkyl$)_2$;

n is 2, 3, 4, 5 or 6;

m is 1, 2, 3, 4, 5 or 6;

p is 0, 1 or 2;

or a pharmaceutically acceptable salt thereof.

5. The compound of claim 4 wherein

X is NH;

R1 is $(C_1\text{-}C_6)$-alkyl;

R2, R2', R3, R3', R4, R4' are, independently of one another, H, F, Cl, Br, I, OH, —(CH$_2$)—OH, CH$_2$F, CHF$_2$, CF$_3$, NO$_2$, N$_3$, CN, S(O)$_p$—R6, $(C_1\text{-}C_6)$-alkylene-S(O)$_p$—R6, COOH, COO$(C_1\text{-}C_6)$alkyl, CONH$_2$,CONH$(C_1\text{-}C_6)$alkyl, CON$[(C_1\text{-}C_6)$alkyl$]_2$, $(C_1\text{-}C_6)$ -alkyl, $(C_2\text{-}C_6)$-alkenyl,$(C_2\text{-}C_6)$-alkynyl, O—$(C_1\text{-}C_6)$-alkyl, where one, more than one, or all hydrogen(s) in the alkyl radicals may be replaced by fluorine;

phenyl, —(CH$_2$)-phenyl, —(CH$_2$)$_n$-phenyl, O-phenyl, O—(CH$_2$)$_m$-phenyl, —(CH$_2$)—O—(CH$_2$)$_m$-phenyl, where the phenyl ring may be substituted one to 3 times by F, Cl, Br, I, OH, CF$_3$, NO$_2$, CN, OCF$_3$, O—$(C_1\text{-}C_6)$-alkyl, $(C_1\text{-}C_6)$-alkyl, NH$_2$, NH$(C_1\text{-}C_6)$-alkyl, N$((C_1\text{-}C_6)$-alkyl$)_2$, SO$_2$—CH$_3$, COOH, COO—$(C_1\text{-}C_6)$-alkyl or CONH$_2$;

R5, R5' are, independently of one another, H, —(CH$_2$)—OH, CH$_2$CH$_2$F, CHF$_2$, CF$_3$, S(O)$_p$—R6, $(C_1\text{-}C_6)$-alkylene-S(O)$_p$—R6, COOH, COO$(C_1\text{-}C_6)$alkyl, CONH$_2$, CONH$(C_1\text{-}C_6)$alkyl, CON$[(C_1\text{-}C_6)$alkyl$]_2$, $(C_1\text{-}C_6)$-alkyl, $(C_2\text{-}C_6)$-alkenyl, $(C_2\text{-}C_6)$-alkynyl, O—$(C_1\text{-}C_6)$-alkyl, where one, more than one, or all hydrogen(s) in the alkyl radicals may be replaced by fluorine;

phenyl, —(CH$_2$)-phenyl, —(CH$_2$)$_n$-phenyl, O-phenyl, O—(CH$_2$)$_m$-phenyl, —(CH$_2$)—O—(CH$_2$)$_m$-phenyl, where the phenyl ring may be substituted one to 3 times by F, Cl, Br, I, OH, CF$_3$, NO$_2$, CN, OCF$_3$, O—$(C_1\text{-}C_6)$-alkyl, $(C_1\text{-}C_6)$-alkyl, NH$_2$, NH$(C_1\text{-}C_6)$-alkyl, N$((C_1\text{-}C_6)$-alkyl$)_2$, SO$_2$—CH$_3$, COOH, COO—$(C_1\text{-}C_6)$-alkyl or CONH$_2$;

wherein at least one of the radicals R2, R2', R3, R3', R4, R4' has the meaning of fluorine or R5, R5' has the meaning of CH$_2$F, CHF$_2$ or CF$_3$;

R6 is H, OH, $(C_1\text{-}C_6)$-alkyl, NH$_2$, NH$(C_1\text{-}C_6)$-alkyl or N$((C_1\text{-}C_6)$-alkyl$)_2$;

n is 2, 3, 4, 5 or 6;

m is 1, 2, 3, 4, 5 or 6;

p is 0, 1 or 2;

or a pharmaceutically acceptable salt thereof.

6. The compound of claim 5 wherein
X is NH;
R1 is $(C_1-C_6)$-alkyl;
R4 is F;
R4' is H or F;
R2, R2', R3, R3' are, independently of one another, H, F, Cl, Br, I, OH, —$(CH_2)$—OH, $CH_2F$, $CHF_2$, $CF_3$, $NO_2$, $N_3$, CN, $S(O)_p$—R6, $(C_1-C_6)$-alkylene-$S(O)_p$—R6, COON, COO$(C_1-C_6)$alkyl, $CONH_2$, CONH$(C_1-C_6)$alkyl, CON[$(C_1-C_6)$alkyl]$_2$, $(C_1-C_6)$-alkyl, $(C_2-C_6)$-alkenyl, $(C_2-C_6)$-alkynyl, O—$(C_1-C_6)$-alkyl, where one, more than one, or all hydrogen(s) in the alkyl radicals may be replaced by fluorine;
phenyl, —$(CH_2)$-phenyl, —$(CH_2)_n$-phenyl, O-phenyl, O—$(CH_2)_m$-phenyl, —$(CH_2)$—O—$(CH_2)_m$-phenyl, where the phenyl ring may be substituted one to 3 times by F, Cl, Br, I, OH, $CF_3$, $NO_2$, CN, $OCF_3$, O—$(C_1-C_6)$-alkyl, $(C_1-C_6)$-alkyl, $NH_2$, NH$(C_1-C_6)$-alkyl, N(($C_1-C_6)$-alkyl)$_2$, $SO_2$—$CH_3$, COOH, COO—$(C_1-C_6)$-alkyl or $CONH_2$;
R5, R5' are, independently of one another, H, —$(CH_2)$—OH, $CH_2F$, $CHF_2$, $CF_3$, $S(O)_p$—R6, $(C_1-C_6)$-alkylene-$S(O)_p$—R6, COOH, COO$(C_1-C_6)$alkyl, $CONH_2$, CONH$(C_1-C_6)$alkyl, CON[$(C_1-C_6)$alkyl]$_2$, $(C_1-C_6)$-alkyl, $(C_2-C_6)$-alkenyl, $(C_2-C_6)$-alkynyl, O—$(C_1-C_6)$-alkyl, where one, more than one, or all hydrogen(s) in the alkyl radicals may be replaced by fluorine;
phenyl, —$(CH_2)$-phenyl, —$(CH_2)_n$-phenyl, O-phenyl, O—$(CH_2)_m$-phenyl, —$(CH_2)$—O—$(CH_2)_m$-phenyl, where the phenyl ring may be substituted one to 3 times by F, Cl, Br, I, OH, $CF_3$, $NO_2$, CN, $OCF_3$, O—$(C_1-C_6)$-alkyl, $(C_1-C_6)$-alkyl, $NH_2$, NH$(C_1-C_6)$-alkyl, N(($C_1-C_6)$-alkyl)$_2$, $SO_2$—$CH_3$, COOH, COO—$(C_1-C_6)$-alkyl or $CONH_2$;
R6 is H, OH, $(C_1-C_6)$-alkyl, $NH_2$, NH$(C_1-C_6)$-alkyl or N(($C_1-C_6)$-alkyl)$_2$;
n is 2, 3, 4, 5 or 6;
m is 1, 2, 3, 4, 5 or 6;
p is 0, 1 or 2;
or a pharmaceutically acceptable salt thereof.

7. The compound of claim 6 wherein
X is NH;
R1 is $(C_1-C_6)$-alkyl;
R4 is F;
R4' is H or F;
R2, R3 is OH;
R2', R3' is H;
R5 is —$(CH_2)$—OH, $CH_2F$, $CHF_2$, $CF_3$, $S(O)_p$—R6($C_1-C_6)$-alkylene-$S(O)_p$—R6, COOH, COO$(C_1-C_6)$alkyl, $CONH_2$, CONH$(C_1-C_6)$alkyl, CON[$(C_1-C_6)$alkyl]$_2$, $(C_1-C_6)$-alkyl, $(C_2-C_6)$-alkenyl, $(C_2-C_6)$-alkynyl, O—$(C_1-C_6)$-alkyl, where one, more than one, or all hydrogen(s) in the alkyl radicals may be replaced by fluorine;
R5' is H;
R6 is H, OH, $(C_1-C_6)$-alkyl, $NH_2$, NH$(C_1-C_6)$-alkyl or N(($C_1-C_6)$-alkyl)$_2$;
n is 2, 3, 4, 5 or 6;
m is 1, 2, 3, 4, 5 or 6;
p is 0, 1 or 2;
or a pharmaceutically acceptable salt thereof.

8. A pharmaceutical composition comprising a compound or pharmaceutically acceptable salt thereof of claim 1.

9. The pharmaceutical composition of claim 8 comprising at least one further active ingredient.

10. The pharmaceutical composition of claim 9 wherein said further active ingredient is a compound which normalizes lipid metabolism.

11. The pharmaceutical composition of claim 9 wherein said further active ingredient is selected from the group consisting of antidiabetics, hypoglycemic active ingredients, HMGCoA reductase inhibitors, cholesterol absorption inhibitors, PPAR gamma agonists, PPAR alpha agonists, PPAR alpha/gamma agonists, PPAR delta agonists, fibrates, MTP inhibitors, bile acid absorption inhibitors, MTP inhibitors, CETP inhibitors, polymeric bile acid adsorbents, LDL receptor inducers, ACAT inhibitors, antioxidants, lipoprotein lipase inhibitors, ATP-citrate lyase inhibitors, squalene synthetase inhibitors, lipoprotein(a) antagonists, HM74A receptor agonists, lipase inhibitors, insulins, sulfonylureas, biguanides, meglitinides, thiazolidinediones, α-glucosidase inhibitors, active ingredients which act on the ATP-dependent potassium channel of the beta cells, glycogen phosphorylase inhibitors, glucagon receptor antagonists, activators of glucokinase, inhibitors of gluconeogenesis, inhibitors of fructose-1,6-bisphosphatase, modulators of glucose transporter 4, inhibitors of glutamine-fructose-6-phosphate amidotransferase, inhibitors of dipeptidylpeptidase IV, inhibitors of 11-beta-hydroxysteroid dehydrogenase 1, inhibitors of protein tyrosine phosphatase 1B, modulators of the sodium-dependent glucose transporter 1 or 2, modulators of GPR40, inhibitors of hormone-sensitive lipase, inhibitors of acetyl-CoA carboxylase, inhibitors of phosphoenolpyruvate carboxykinase, inhibitors of glycogen synthase kinase-3 beta, inhibitors of protein kinase C beta, endothelin-A receptor antagonists, inhibitors of I kappaB kinase, modulators of the glucocorticoid receptor, CART agonists, NPY agonists, MC4 agonists, orexin agonists, H3 agonists, TNF agonists, CRF agonists, CRF BP antagonists, urocortin agonists, β3 agonists, CB1 receptor antagonists, MSH (melanocyte-stimulating hormone) agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, uncoupling protein 2 or 3 modulators, leptin agonists, DA agonists (bromocriptine, Doprexin), lipase/amylase inhibitors, PPAR modulators, RXR modulators or TR-β agonists or amphetamines.

12. The pharmaceutical composition of claim 8 which comprises as further excipient one or more metal salts.

13. A method of treating lipid metabolism disorders comprising administering to a patient in need thereof a therapeutically effective amount of a compound of claim 1 or a pharmaceutically acceptable salt thereof.

14. A method of treating hyperlipidemia comprising administering to a patient in need thereof a therapeutically effective amount of a compound of claim 1 or a pharmaceutically acceptable salt thereof.

15. A method of lowering the serum cholesterol level comprising administering to a patient in need thereof a therapeutically effective amount of a compound of claim 1 or a pharmaceutically acceptable salt thereof.

16. A method of treating arteriosclerotic manifestations comprising administering to a patient in need thereof a therapeutically effective amount of a compound of claim 1 or a pharmaceutically acceptable salt thereof.

17. A method of treating insulin resistance comprising administering to a patient in need thereof a therapeutically effective amount of a compound of claim 1 or a pharmaceutically acceptable salt thereof.

18. A method of treating diabetes comprising administering to a patient in need thereof a therapeutically effective amount of a compound of claim 1 or a pharmaceutically acceptable salt thereof.

\* \* \* \* \*